US011771901B2

(12) United States Patent
Rondoni et al.

(10) Patent No.: US 11,771,901 B2
(45) Date of Patent: Oct. 3, 2023

(54) MICROSTIMULATION SLEEP DISORDERED BREATHING (SDB) THERAPY DEVICE

(71) Applicant: INSPIRE MEDICAL SYSTEMS, INC., Golden Valley, MN (US)

(72) Inventors: John Rondoni, Plymouth, MN (US); David Dieken, Minneapolis, MN (US); Kevin Verzal, Lino Lakes, MN (US)

(73) Assignee: INSPIRE MEDICAL SYSTEMS, INC., Golden Valley, MN (US)

( * ) Notice: Subject to any disclaimer, the term of this patent is extended or adjusted under 35 U.S.C. 154(b) by 0 days.

(21) Appl. No.: 17/525,458

(22) Filed: Nov. 12, 2021

(65) Prior Publication Data

US 2022/0212006 A1    Jul. 7, 2022

Related U.S. Application Data

(63) Continuation of application No. 15/774,471, filed as application No. PCT/US2016/062546 on Nov. 17, 2016, now abandoned.

(Continued)

(51) Int. Cl.
*A61N 1/05* (2006.01)
*A61N 1/36* (2006.01)
(Continued)

(52) U.S. Cl.
CPC .......... *A61N 1/3611* (2013.01); *A61N 1/0551* (2013.01); *A61N 1/0558* (2013.01);
(Continued)

(58) Field of Classification Search
CPC .. A61N 1/3611; A61N 1/0551; A61N 1/0558; A61N 1/36139; A61N 1/3614;
(Continued)

(56) References Cited

U.S. PATENT DOCUMENTS 3,456,134 A    7/1969    Ko
3,563,245 A    2/1971    McLean
(Continued)

FOREIGN PATENT DOCUMENTS

EP    1175919    1/2002
JP    2007281015    10/2007
(Continued)

OTHER PUBLICATIONS

US 8,886,318 B2, 11/2014, Jacobson et al. (withdrawn)
(Continued)

*Primary Examiner* — Carl H Layno
*Assistant Examiner* — Anh-Khoa N Dinh
(74) *Attorney, Agent, or Firm* — Dicke, Billig & Czaja, PLLC

(57) ABSTRACT

An apparatus includes an implantable stimulator to treat sleep disordered breathing (SDB) and at least one electrode associated with the stimulator. The apparatus includes a therapy device arranged to be implanted within a head/neck region of a patient. The therapy device includes a microstimulator including a housing to encapsulate at least stimulation circuitry, a rechargeable power element, and a control portion including a therapy manager to control the stimulation circuitry.

15 Claims, 20 Drawing Sheets

Related U.S. Application Data

(60) Provisional application No. 62/256,680, filed on Nov. 17, 2015.

(51) Int. Cl.
*A61N 1/372* (2006.01)
*A61N 1/378* (2006.01)

(52) U.S. Cl.
CPC ....... *A61N 1/3614* (2017.08); *A61N 1/36139* (2013.01); *A61N 1/3787* (2013.01); *A61N 1/37205* (2013.01)

(58) Field of Classification Search
CPC .............. A61N 1/37205; A61N 1/3787; A61N 1/3601; A61N 1/0531; A61N 1/0534; A61N 1/36046; A61N 1/3606; A61N 1/36064; A61N 1/36067; A61N 1/36071; A61N 1/372; A61P 11/00; A61P 11/16; A61B 2562/046; A61B 2562/164; A61B 5/24; A61B 5/282; A61B 5/291; A61B 5/686; A61B 2017/00269
See application file for complete search history.

(56) References Cited

U.S. PATENT DOCUMENTS

| | | | |
|---|---|---|---|
| 3,659,615 A | 5/1972 | Enger | |
| 3,693,625 A | 9/1972 | Auphan | |
| 3,807,411 A | 4/1974 | Harris et al. | |
| 4,119,103 A | 10/1978 | Jirak | |
| 4,613,784 A | 9/1986 | Haun et al. | |
| 4,690,143 A | 9/1987 | Schroeppel | |
| 4,780,638 A | 10/1988 | Reinelt et al. | |
| 4,798,206 A | 1/1989 | Maddison et al. | |
| 5,193,540 A | 3/1993 | Schulman et al. | |
| 5,314,451 A | 5/1994 | Mulier | |
| 5,324,316 A | 6/1994 | Schulman | |
| 5,358,514 A | 10/1994 | Schulman et al. | |
| 5,411,538 A | 5/1995 | Lin | |
| 5,431,694 A | 6/1995 | Snaper et al. | |
| 5,489,225 A | 2/1996 | Julian | |
| 5,615,466 A | 4/1997 | Safari et al. | |
| 5,869,189 A | 2/1999 | Hagood, IV et al. | |
| 5,906,634 A | 5/1999 | Flynn et al. | |
| 6,131,581 A | 10/2000 | Leysieffer et al. | |
| 6,185,452 B1 | 2/2001 | Schulman et al. | |
| 6,240,316 B1 | 5/2001 | Richmond et al. | |
| 6,269,266 B1 | 7/2001 | Leysieffer | |
| 6,337,835 B1 | 1/2002 | Sporn et al. | |
| 6,442,413 B1 | 8/2002 | Silver | |
| 6,470,212 B1 | 10/2002 | Weijand et al. | |
| 6,636,767 B1 | 10/2003 | Knudson et al. | |
| 6,764,446 B2 | 7/2004 | Wolinsky et al. | |
| 6,822,343 B2 | 11/2004 | Estevez | |
| 6,899,976 B2 | 5/2005 | Larson et al. | |
| 6,963,157 B2 | 11/2005 | Sato et al. | |
| 7,054,692 B1 | 5/2006 | Whitehurst | |
| 7,084,605 B2 | 8/2006 | Mickle et al. | |
| 7,130,681 B2 | 10/2006 | Gebhardt et al. | |
| 7,283,874 B2 | 10/2007 | Penner | |
| 7,292,888 B2 | 11/2007 | Deno et al. | |
| 7,365,455 B2 | 4/2008 | Hamel et al. | |
| 7,442,465 B2 | 10/2008 | Kim et al. | |
| 7,530,956 B2 | 5/2009 | Lewicke et al. | |
| 7,620,451 B2 | 11/2009 | Demarais et al. | |
| 7,629,727 B2 | 12/2009 | Whinnery | |
| 7,640,061 B2 | 12/2009 | He et al. | |
| 7,649,305 B2 | 1/2010 | Priya et al. | |
| 7,734,343 B2 | 6/2010 | Ransbury | |
| 7,881,796 B2 | 2/2011 | Scott et al. | |
| 7,896,813 B2 | 3/2011 | Sowelam et al. | |
| 8,039,834 B2 | 10/2011 | Wang et al. | |
| 8,108,045 B2 | 1/2012 | Biggs, Jr. et al. | |
| 8,204,595 B2 | 6/2012 | Pianca et al. | |
| 8,224,449 B2 | 7/2012 | Carbunaru et al. | |
| 8,311,632 B2 | 11/2012 | Pless et al. | |
| 8,352,025 B2 | 1/2013 | Jacobson | |
| 8,359,098 B2 | 1/2013 | Lund et al. | |
| 8,406,877 B2 | 3/2013 | Smith et al. | |
| 8,433,409 B2 | 4/2013 | Johnson et al. | |
| 8,506,495 B2 | 8/2013 | Mi et al. | |
| 8,527,068 B2 | 9/2013 | Ostroff | |
| 8,666,497 B2 | 3/2014 | Janzig et al. | |
| 8,670,823 B2 | 3/2014 | Murtonen | |
| 8,682,438 B2 | 3/2014 | Schliecher et al. | |
| 8,777,863 B2 | 7/2014 | Piaget et al. | |
| 8,923,963 B2 | 12/2014 | Bonner et al. | |
| 9,002,470 B2 | 4/2015 | Reinke et al. | |
| 9,078,610 B2 | 7/2015 | McKenna | |
| 9,084,859 B2 | 7/2015 | Connor | |
| 9,149,644 B2 | 10/2015 | Biggs, Jr. et al. | |
| 9,168,383 B2 | 10/2015 | Jacobson et al. | |
| 9,216,285 B1 | 12/2015 | Boling et al. | |
| 9,220,911 B2 | 12/2015 | Gordon et al. | |
| 9,276,348 B1 | 3/2016 | Vadlamudi et al. | |
| 9,364,675 B2 | 6/2016 | Deterre et al. | |
| 9,398,901 B2 | 7/2016 | Tischendorf et al. | |
| 9,616,242 B2 | 4/2017 | Imran | |
| 9,662,066 B2 | 5/2017 | Ledet et al. | |
| 9,821,159 B2 | 11/2017 | Ackermann et al. | |
| 9,889,299 B2 | 2/2018 | Ni | |
| 9,956,398 B2 | 5/2018 | Callegari et al. | |
| 10,195,428 B2 | 2/2019 | Scheiner | |
| 10,716,947 B2 | 7/2020 | Sheldon et al. | |
| 2001/0010010 A1* | 7/2001 | Richmond ........... A61N 1/3601 607/42 |
| 2002/0011300 A1 | 1/2002 | Cass | |
| 2002/0053801 A1 | 5/2002 | Herman | |
| 2002/0183791 A1 | 12/2002 | Denker | |
| 2003/0056351 A1 | 3/2003 | Wilkie et al. | |
| 2003/0141785 A1 | 7/2003 | Sato et al. | |
| 2003/0153953 A1 | 8/2003 | Park | |
| 2003/0171783 A1 | 9/2003 | Tsukamoto et al. | |
| 2004/0073267 A1 | 4/2004 | Holzer | |
| 2004/0153127 A1 | 8/2004 | Gordon et al. | |
| 2004/0185337 A1 | 9/2004 | Ishizaki | |
| 2005/0012434 A1 | 1/2005 | Pizzochero et al. | |
| 2005/0021100 A1 | 1/2005 | Tsukamoto et al. | |
| 2005/0021108 A1 | 1/2005 | Klosterman et al. | |
| 2005/0080349 A1 | 4/2005 | Okada et al. | |
| 2005/0080472 A1 | 4/2005 | Atkinson | |
| 2005/0085874 A1 | 4/2005 | Davis et al. | |
| 2005/0110277 A1 | 5/2005 | Adamson et al. | |
| 2005/0165465 A1* | 7/2005 | Pianca ................. H01R 43/16 607/116 |
| 2005/0251216 A1 | 11/2005 | Hill | |
| 2005/0267547 A1 | 12/2005 | Knudson et al. | |
| 2005/0274176 A1 | 12/2005 | Thiesen et al. | |
| 2006/0009830 A1 | 1/2006 | Atkinson | |
| 2006/0020297 A1 | 1/2006 | Gerber et al. | |
| 2006/0136004 A1 | 6/2006 | Cowan | |
| 2006/0167523 A1 | 7/2006 | Tehrani | |
| 2006/0184204 A1 | 8/2006 | He | |
| 2006/0184206 A1 | 8/2006 | Baker, III et al. | |
| 2006/0217776 A1 | 9/2006 | White et al. | |
| 2006/0252976 A1 | 11/2006 | Rosero | |
| 2007/0007473 A1 | 1/2007 | Kumagai | |
| 2007/0049842 A1 | 3/2007 | Hill et al. | |
| 2007/0078492 A1 | 4/2007 | Tozzi et al. | |
| 2007/0118183 A1 | 5/2007 | Gelfand et al. | |
| 2007/0150020 A1 | 6/2007 | Hokanson et al. | |
| 2007/0173893 A1 | 6/2007 | Pitts | |
| 2007/0179581 A1 | 8/2007 | Dennis et al. | |
| 2007/0255379 A1 | 11/2007 | Williams | |
| 2007/0284969 A1 | 12/2007 | Xu | |
| 2007/0288077 A1 | 12/2007 | Bulkes et al. | |
| 2007/0293904 A1 | 12/2007 | Gelbart et al. | |
| 2008/0004904 A1 | 1/2008 | Tran | |
| 2008/0039904 A1 | 2/2008 | Bulkes | |
| 2008/0067618 A1 | 3/2008 | Wang et al. | |
| 2008/0103407 A1 | 5/2008 | Bolea | |
| 2008/0103545 A1 | 5/2008 | Bolea | |
| 2008/0109044 A1 | 5/2008 | Gramse et al. | |

(56) References Cited

U.S. PATENT DOCUMENTS

| | | |
|---|---|---|
| 2008/0119421 A1 | 5/2008 | Tuszynski et al. |
| 2008/0119911 A1 | 5/2008 | Rosero |
| 2008/0136292 A1 | 6/2008 | Thiesen |
| 2008/0150396 A1 | 6/2008 | Clingman et al. |
| 2008/0200963 A1 | 8/2008 | Pless et al. |
| 2008/0203849 A1 | 8/2008 | Hagg |
| 2008/0262562 A1 | 10/2008 | Roberts et al. |
| 2008/0312720 A1 | 12/2008 | Tran et al. |
| 2008/0312725 A1 | 12/2008 | Penner |
| 2009/0025773 A1 | 1/2009 | Stark |
| 2009/0152990 A1 | 6/2009 | Brown et al. |
| 2009/0160292 A1 | 6/2009 | Whinnery |
| 2009/0167034 A1 | 7/2009 | Waters et al. |
| 2009/0167110 A1 | 7/2009 | Berkcan et al. |
| 2009/0171404 A1 | 7/2009 | Irani et al. |
| 2009/0171408 A1 | 7/2009 | Solem |
| 2009/0171448 A1 | 7/2009 | Eli |
| 2009/0179523 A1 | 7/2009 | Wang et al. |
| 2009/0216292 A1 | 8/2009 | Pless et al. |
| 2010/0049269 A1 | 2/2010 | Tran et al. |
| 2010/0063557 A1 | 3/2010 | Imran |
| 2010/0076517 A1 | 3/2010 | Imran |
| 2010/0117488 A1 | 5/2010 | Wang et al. |
| 2010/0133954 A1 | 6/2010 | Despesse et al. |
| 2010/0160994 A1 | 6/2010 | Feldman et al. |
| 2010/0171394 A1 | 7/2010 | Glenn et al. |
| 2010/0317929 A1 | 12/2010 | Mi et al. |
| 2010/0317977 A1 | 12/2010 | Piaget et al. |
| 2010/0317978 A1 | 12/2010 | Maile et al. |
| 2011/0034811 A1 | 2/2011 | Naujokat et al. |
| 2011/0077708 A1 | 3/2011 | Ostroff |
| 2011/0152706 A1 | 6/2011 | Christopherson et al. |
| 2011/0202119 A1* | 8/2011 | Ni .................. A61B 5/704 607/116 |
| 2011/0208010 A1 | 8/2011 | McKenna |
| 2012/0089153 A1 | 4/2012 | Christopherson et al. |
| 2012/0089199 A1 | 4/2012 | Bolea et al. |
| 2013/0066393 A1 | 3/2013 | Gross et al. |
| 2013/0085537 A1 | 4/2013 | Mashiach |
| 2013/0231726 A1* | 9/2013 | Johnson ............ A61N 1/37217 607/118 |
| 2014/0330331 A1 | 11/2014 | Thompson-Nauman et al. |
| 2015/0012059 A1 | 1/2015 | Kim et al. |
| 2015/0073247 A1 | 3/2015 | Gordon et al. |
| 2015/0105836 A1 | 4/2015 | Bonner et al. |
| 2015/0224325 A1 | 8/2015 | Imran |
| 2016/0067497 A1 | 3/2016 | Levine et al. |
| 2020/0147377 A1 | 5/2020 | Hoffer |

FOREIGN PATENT DOCUMENTS

| | | |
|---|---|---|
| WO | 98/43700 | 10/1998 |
| WO | 20060244868 | 3/2006 |
| WO | 2007059343 | 5/2007 |
| WO | WO2007059343 | 5/2007 |
| WO | 2007068284 | 6/2007 |
| WO | 2007080487 A1 | 7/2007 |
| WO | 2007109272 | 9/2007 |
| WO | 2007149462 | 12/2007 |
| WO | 2008085886 | 7/2008 |
| WO | 2009048385 A1 | 4/2009 |
| WO | 2010030700 | 3/2010 |
| WO | 2010039853 A1 | 4/2010 |
| WO | 2012112186 | 8/2012 |
| WO | 2013067496 | 5/2013 |
| WO | 2014169145 A1 | 10/2014 |
| WO | 2015200720 | 12/2015 |

OTHER PUBLICATIONS

Loeb, Gerald E., et al. "BION TM System for Distributed Neural Prosthetic Interfaces." Medical Engineering & Physics, vol. 23, No. 1, 2001, pp. 9-18, https://doi.org/10.1016/S1350-4533(01)00011-X. (Year: 2001).*

Boston Scientific, Precision Spectra™ System Implantable Pulse Generator, Directions for Use, 2015, 18 pages.

Bal Seal Engineering Inc., Next-Generation IPGs Integrate Connector System Components, Sep. 17, 2014, 3 pages.

Bal Seal Engineering Inc., The Technologies behind the Next Generation of Neuromodulation Devices, May 3, 2016, 3 pages.

Medtronic, "Medtronic Announces First Human Implant of World's Smallest, Minimally Invasive Cardiac Pacemaker", Dec. 9, 2013, (2 pages).

Zheng et al., In Vivo Self-Powered Wireless Cardiac Monitoring via Implantable Triboelectric Nanogenerator, ACS Nano, Jun. 2, 2016, pp. 1-2.

Bai et al., Membrane-Based Self-Powered Triboelecliic Sensors for Pressure Change Detection and Its Uses in Security Surveillance and Healthcare Monitoring, Advanced Functional Materials Journal, 2014, pp. 5807-5813.

Ye Ma et al., Self-Powered, One-Stop, and Multifunctional Implantable Triboelectic Active Sensor for Real-Time Biomedical Monitoring, Nano Letters, Sep. 8, 2016, pp. 1-2.

Clark et al., Piezoelectric Energy Harvesting for Bio-MEMS Applications, University of Pittsburgh, 2009, pp. 405-430.

* cited by examiner

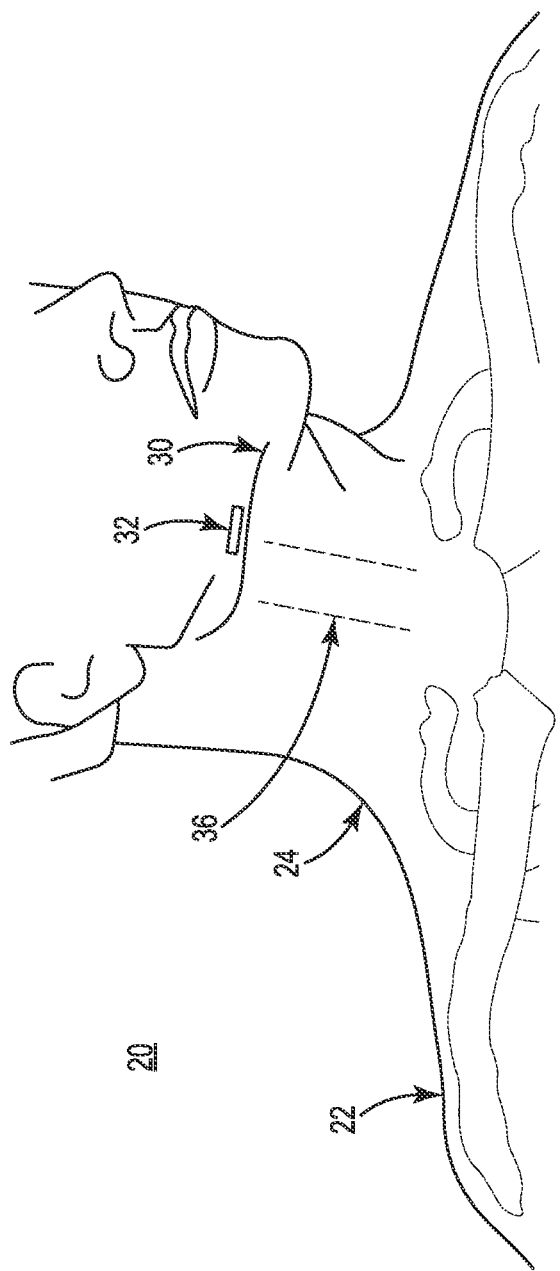
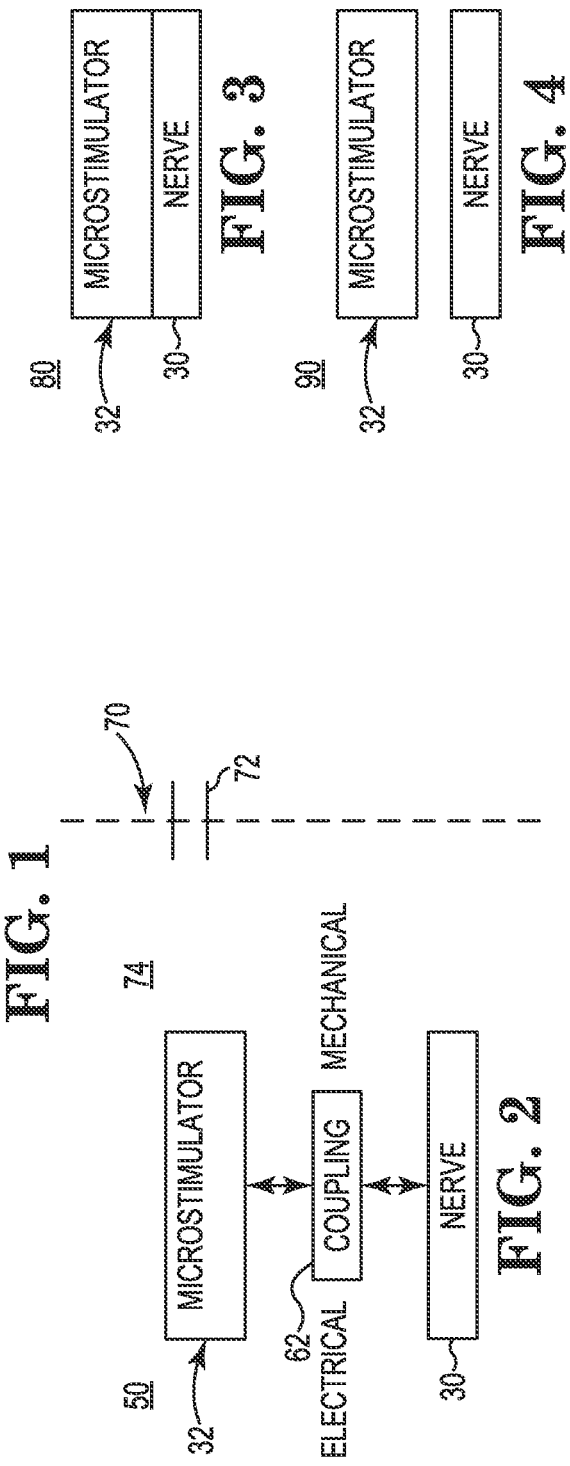

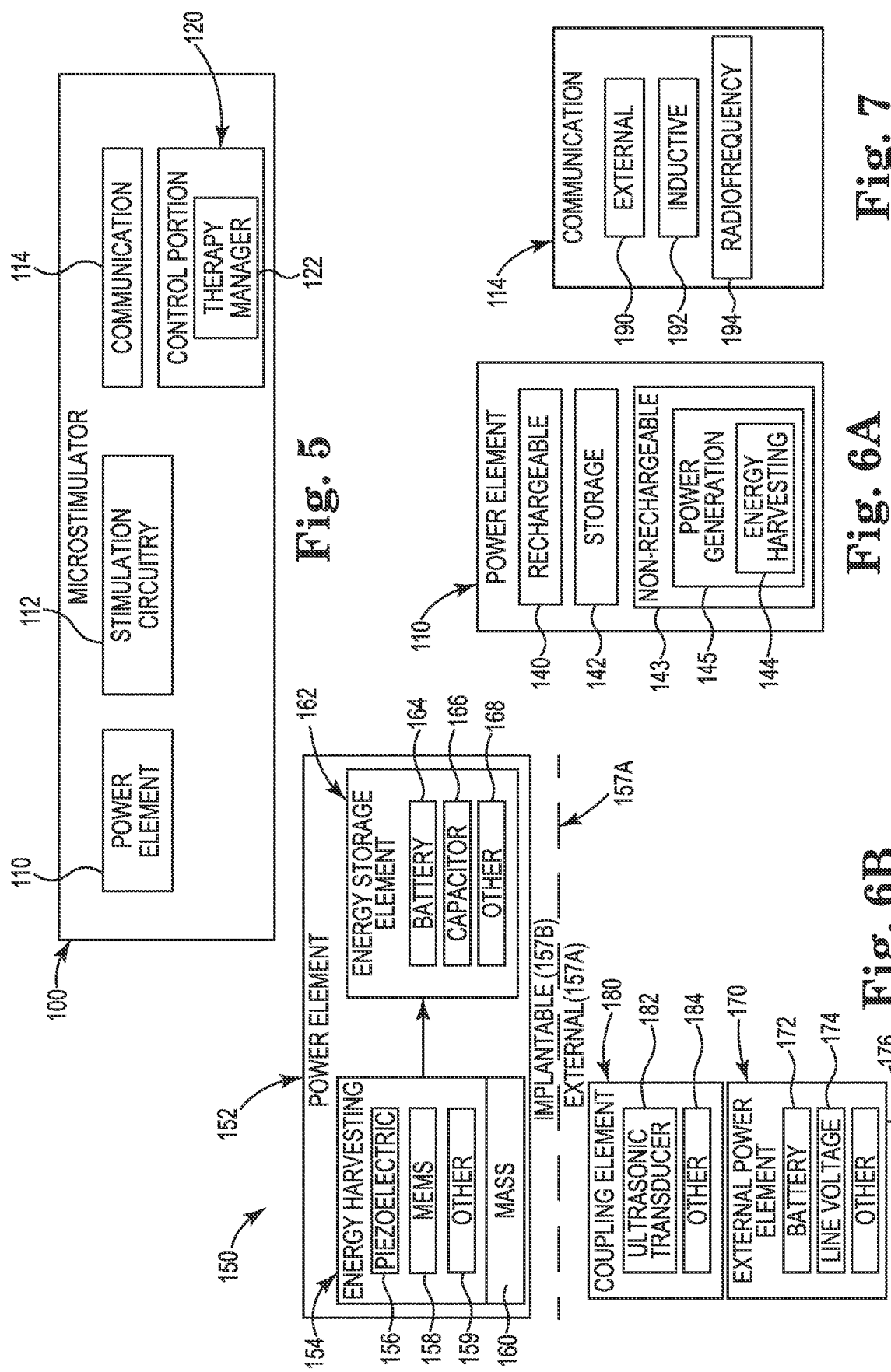

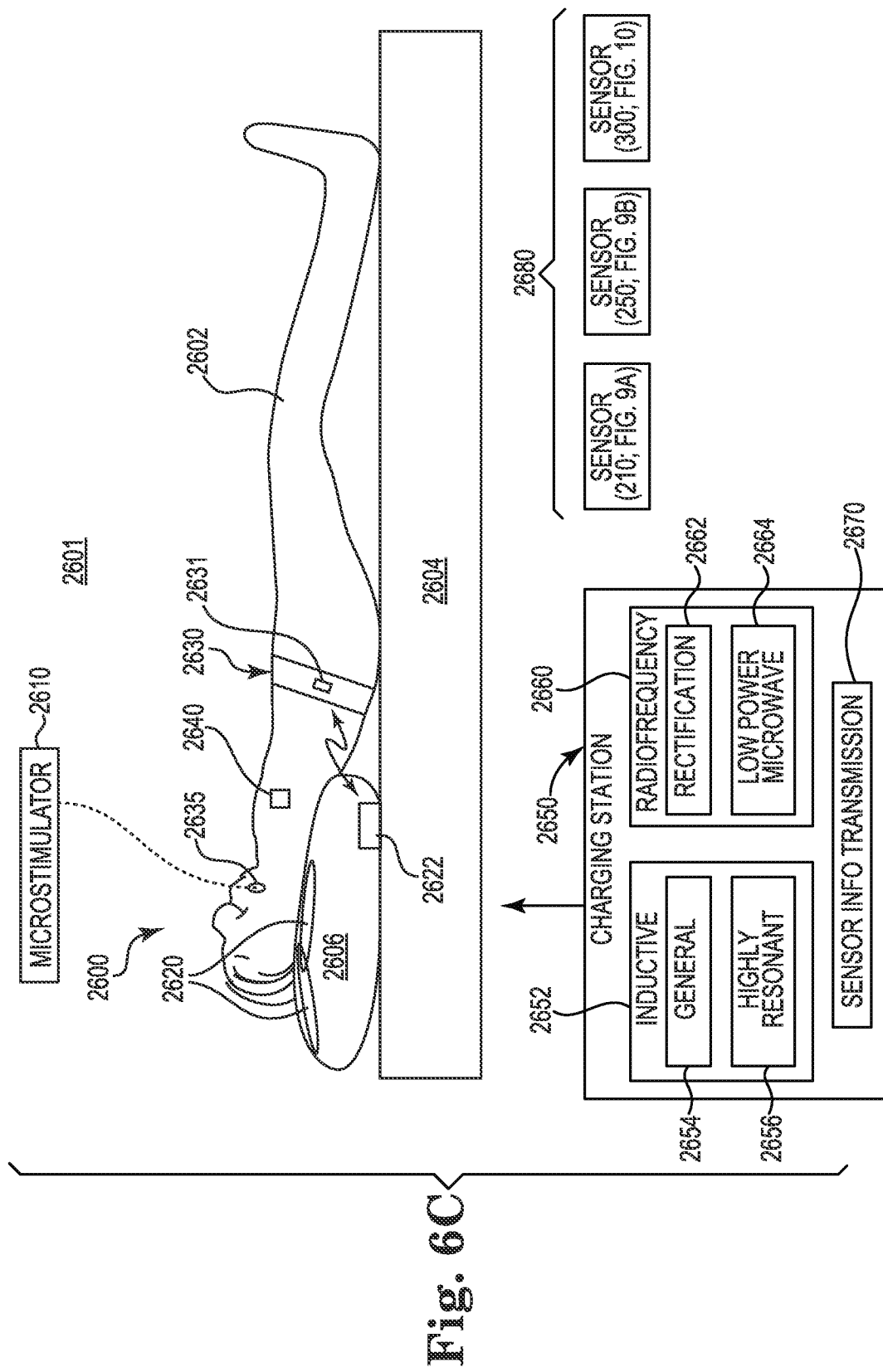

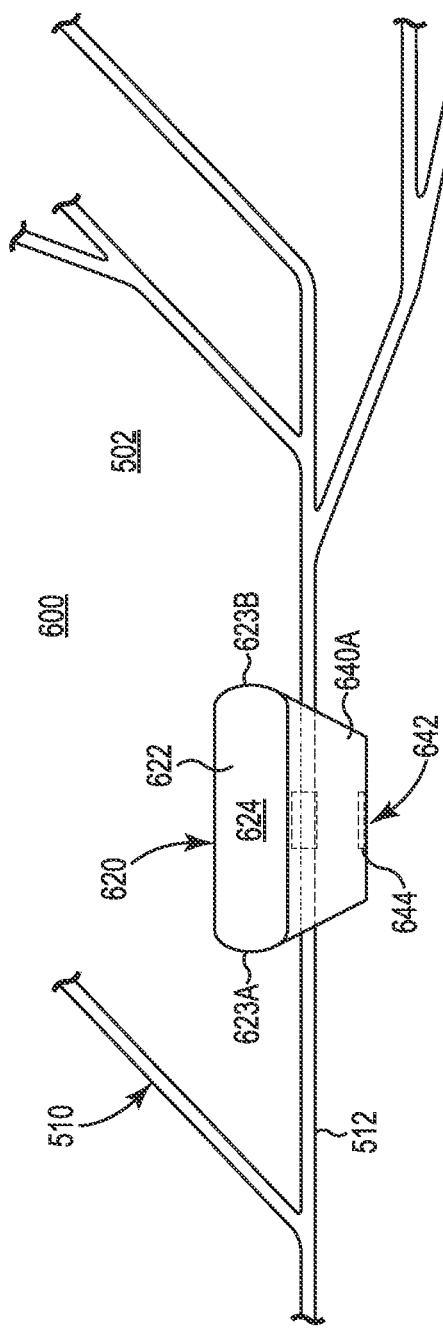
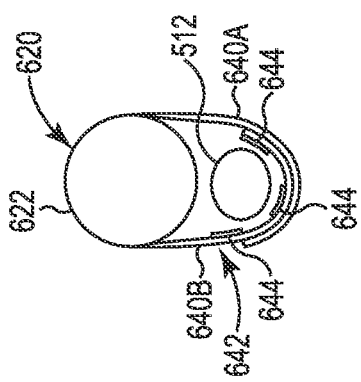
FIG. 15A
FIG. 15B

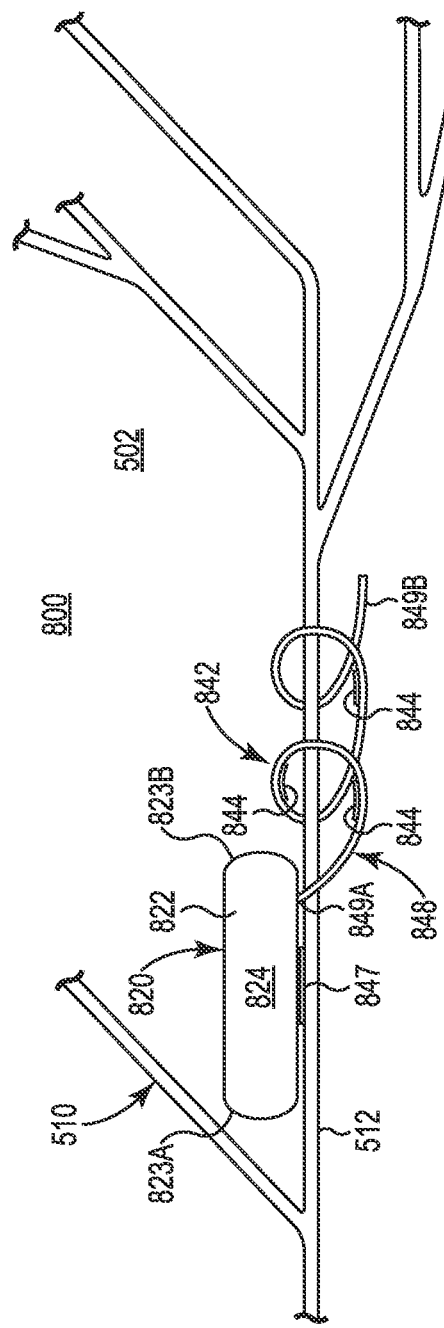
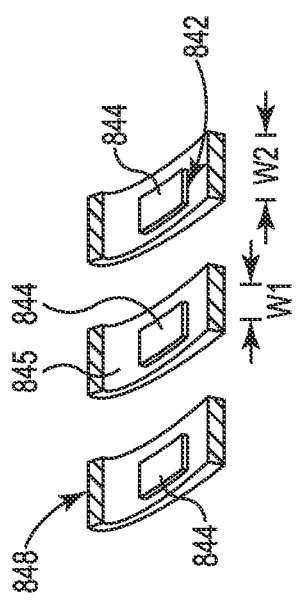
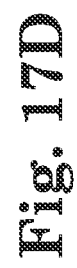
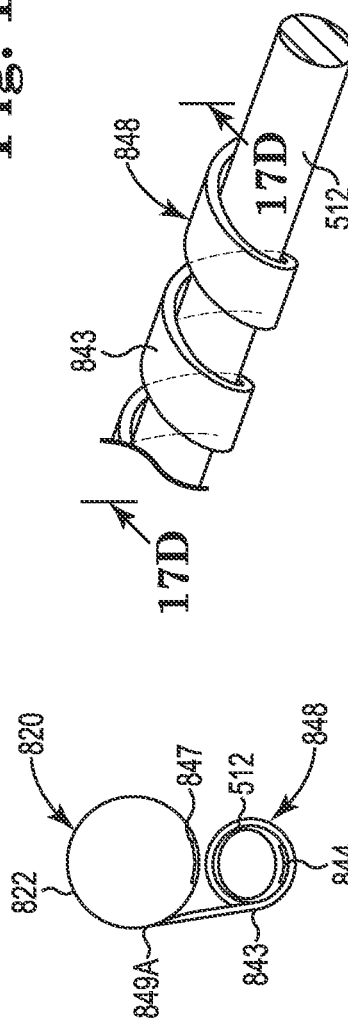
Fig. 17A
Fig. 17B
Fig. 17C
Fig. 17D

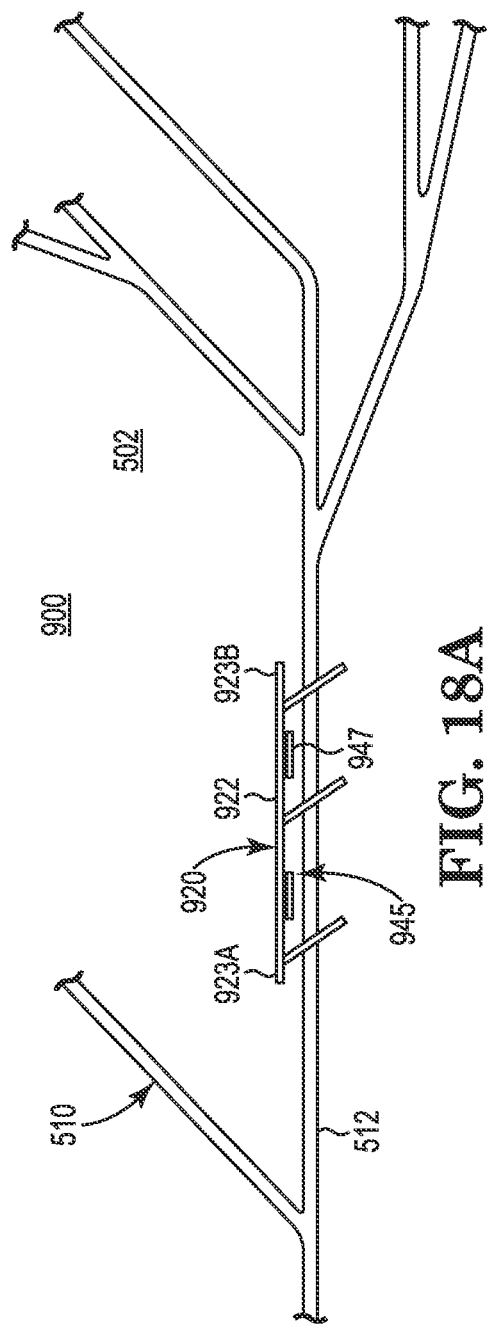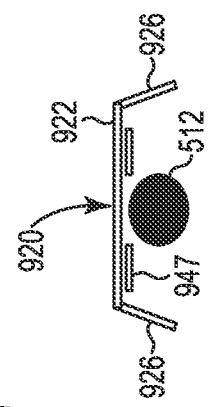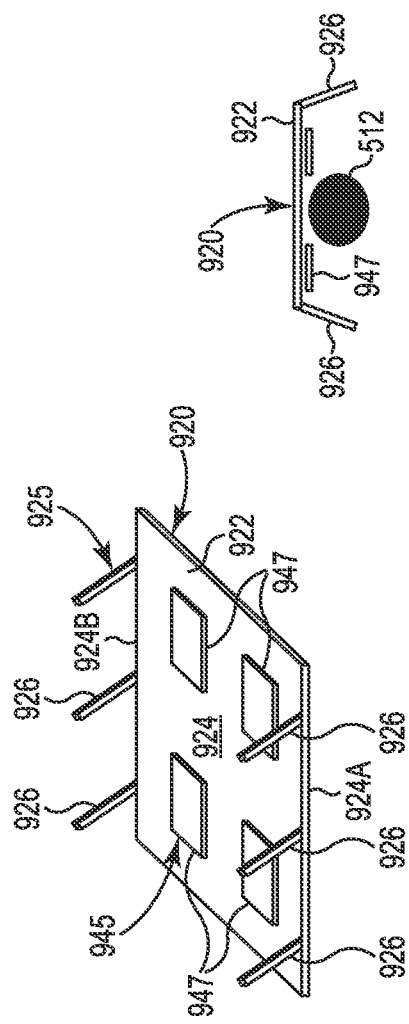

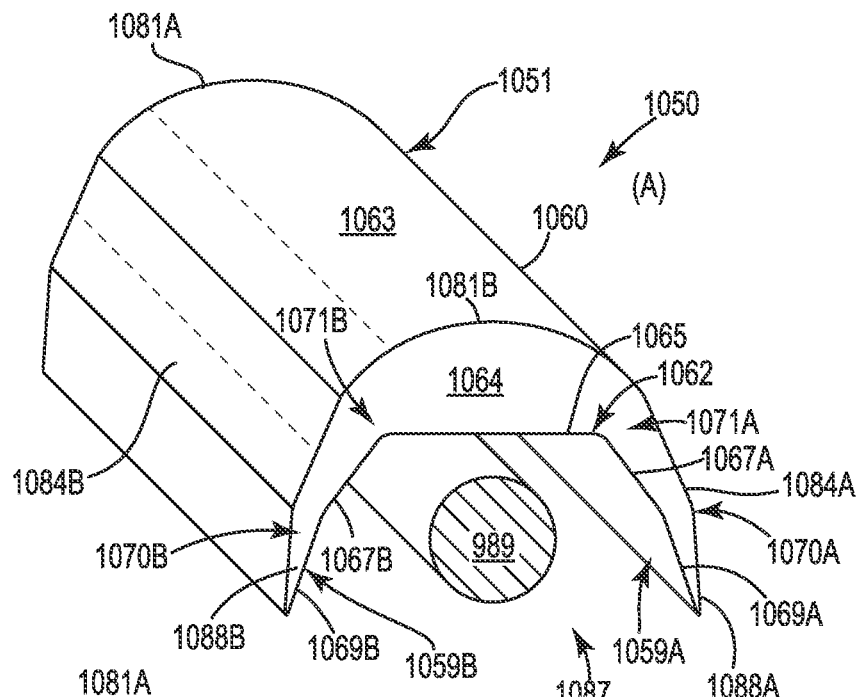
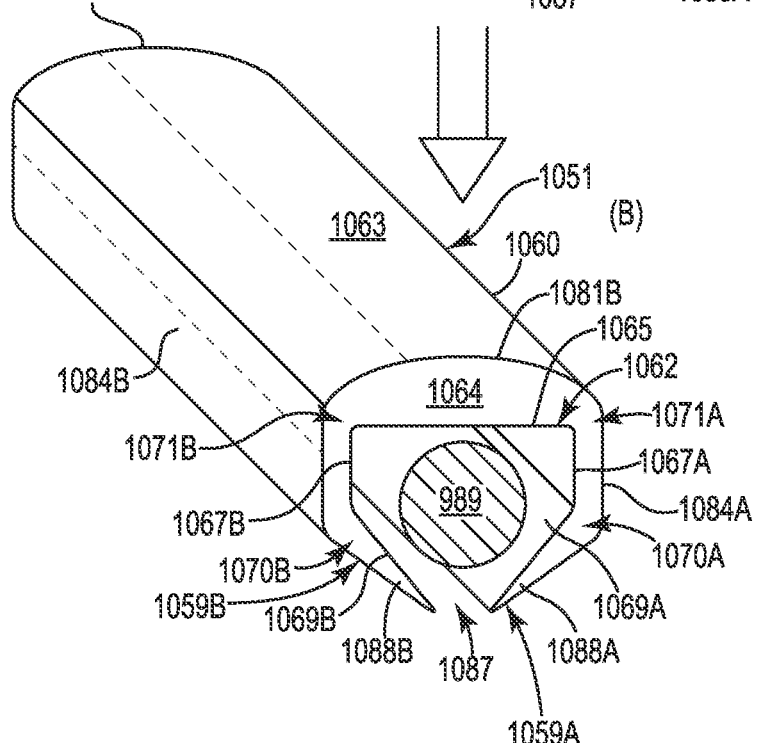
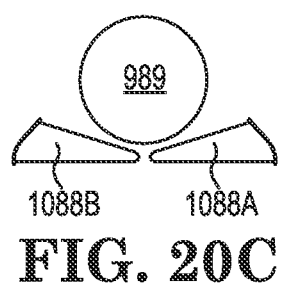
FIG. 20C
FIG. 20B

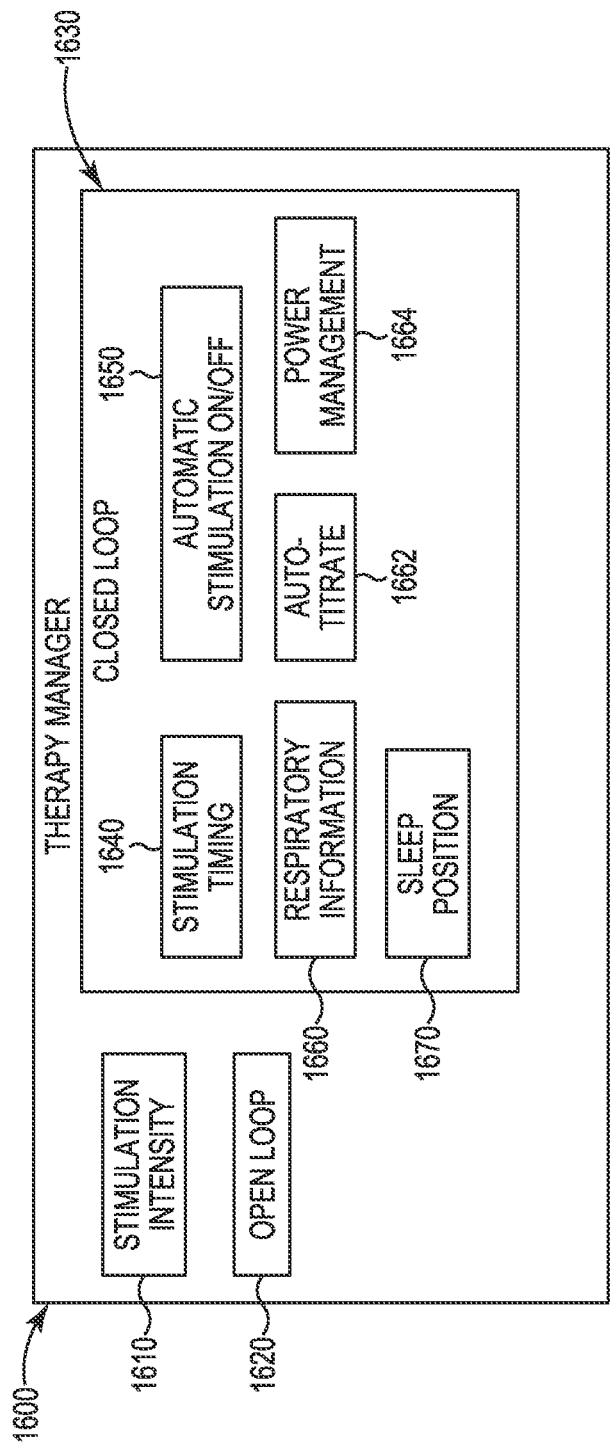
FIG. 24
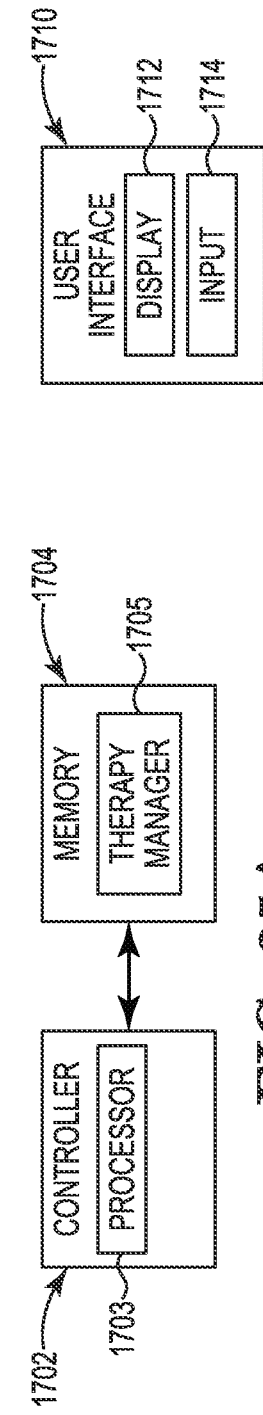
FIG. 25A
FIG. 25B

MICROSTIMULATION SLEEP DISORDERED BREATHING (SDB) THERAPY DEVICE

CROSS-REFERENCE

This application is a continuation of U.S. application Ser. No. 15/774,471, filed May 8, 2018, which is a National Stage Application of, and that claims priority to, PCT Application No. PCT/US2016/062546, entitled "MICROSTIMULATION SLEEP DISORDERED BREATHING (SDB) THERAPY DEVICE" having a filing date of Nov. 17, 2016, which claims the benefit of U.S. Provisional Patent Application No. 62/256,680, entitled "MICROSTIMULATION SLEEP DISORDERED BREATHING (SDB) THERAPY DEVICE," having a filing date of Nov. 17, 2015, all of which are incorporated herein by reference.

BACKGROUND

Treating sleep disordered breathing has led to improved sleep quality for some patients.

BRIEF DESCRIPTION OF THE DRAWINGS

FIG. 1 is a block diagram schematically representing a microstimulation therapy device as implanted within a patient's body, according to one example of the present disclosure.

FIG. 2 is a block diagram schematically representing an implanted microstimulation therapy device, according to one example of the present disclosure.

FIG. 3 is a block diagram schematically representing a microstimulation therapy device juxtaposed relative to a nerve, according to one example of the present disclosure.

FIG. 4 is a block diagram schematically representing a microstimulation therapy device juxtaposed relative to a nerve, according to one example of the present disclosure.

FIG. 5 is a block diagram schematically representing a microstimulator of microstimulation therapy device, according to one example of the present disclosure.

FIG. 6A is a block diagram schematically representing a power element, according to one example of the present disclosure.

FIG. 6B is a block diagram schematically representing an energy harvesting arrangement, according to one example of the present disclosure.

FIG. 6C is a diagram schematically representing at least a charging station in association with a patient support, according to one example of the present disclosure.

FIG. 7 is a block diagram schematically representing a communication element, according to one example of the present disclosure.

FIG. 15A is a diagram schematically representing a microstimulation therapy device implanted relative to a nerve, according to one example of the present disclosure.

FIG. 15B is a sectional view schematically representing the implanted microstimulation therapy device of FIG. 15A, according to one example of the present disclosure.

FIG. 17A is a diagram schematically representing a microstimulation therapy device implanted relative to a nerve, according to one example of the present disclosure.

FIG. 17B is a sectional view schematically representing the implanted microstimulation therapy device of FIG. 17A, according to one example of the present disclosure.

FIG. 17C is a perspective view schematically representing a helically-shaped flange of the therapy device of FIG. 17A-17B, according to one example of the present disclosure.

FIG. 17D is a sectional view as taken along lines 17D-17D of FIG. 17C and schematically representing an axial array of electrodes, according to one example of the present disclosure.

FIG. 18A is a diagram schematically representing a microstimulation therapy device implanted relative to a nerve, according to one example of the present disclosure.

FIG. 18B is a perspective view schematically representing the microstimulation therapy device of FIG. 18A, according to one example of the present disclosure.

FIG. 18C is a sectional view schematically representing the implanted microstimulation therapy device of FIG. 18A, according to one example of the present disclosure.

FIG. 20B is a perspective view schematically representing an electrode cuff for a stimulation therapy device, according to one example of the present disclosure.

FIG. 20C is a partial end view schematically representing an electrode cuff, according to one example of the present disclosure.

FIG. 24 is a block diagram schematically representing a therapy manager, according to one example of the present disclosure.

FIG. 25A is a block diagram schematically representing a control portion, according to one example of the present disclosure.

FIG. 25B is a block diagram schematically representing a user interface, according to one example of the present disclosure.

DETAILED DESCRIPTION

Figure 9A:
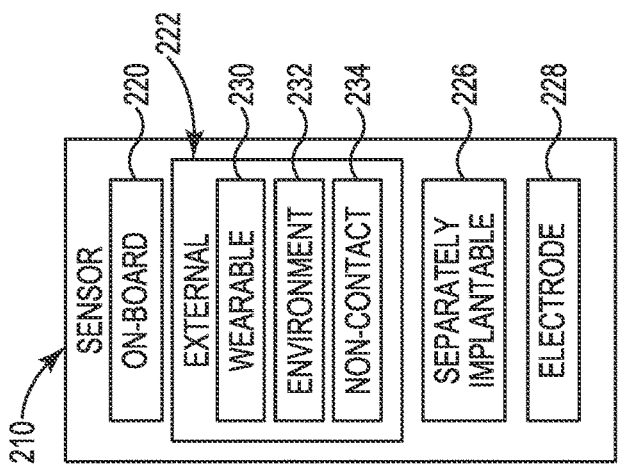
FIG. 9A is a block diagram schematically representing a sensor, according to one example of the present disclosure.

In the following Detailed Description, reference is made to the accompanying drawings which form a part hereof, and in which is shown by way of illustration specific examples of the present disclosure which may be practiced. In this regard, directional terminology, such as "top," "bottom," "front," "back," "leading," "trailing," etc., is used with reference to the orientation of the Figure(s) being described. Because components of at least some examples of the present disclosure can be positioned in a number of different orientations, the directional terminology is used for purposes of illustration and is in no way limiting. It is to be understood that other examples may be utilized and structural or logical changes may be made without departing from the scope of the present disclosure. The following detailed description, therefore, is not to be taken in a limiting sense.

In at least some examples of the present disclosure, an implantable microstimulation therapy device is employed in association with a therapy for sleep disordered breathing. In some examples, the microstimulation therapy device includes a microstimulator defining a housing sized (e.g. a volume) and/or shaped to facilitate a minimally invasive implantation that is performed in close proximity to a nerve to be stimulated by the microstimulator. In some examples, at least the housing of the microstimulator has a volume and a shape to enable the microstimulator to be secured directly against the nerve to be stimulated. In some examples, an electrode structure extends from the housing and is also directly secured against, or at least coupled relative to, the nerve to be stimulated.

In some examples, a housing of the microstimulator has a volume and a shape to enable the microstimulator to be secured against or relative to other body structures in proximity to the nerve to be stimulated while circuitry within the housing is electrically coupled relative to the nerve via an electrode structure extending outwardly from a housing of the microstimulator.

With this in mind, the terms "microstimulation" and/or "microstimulator" refer to the size (e.g. including but not limited to volume) and/or shape of a housing of a therapy device which enable its placement in a minimally invasive manner and/or fixation in close proximity to a target nerve. In some examples, a microstimulator is sized and/or shaped to be fully implantable via a single incision. In some examples, the single incision is located in a head/neck region of the patient. In some examples, the housing of the microstimulator has a volume at least one order of magnitude less than a volume of commercially available, pectorally implantable pulse generator, such as traditional pacemakers, cardio-defibrillators, etc. In some examples, the housing of the microstimulator has a volume at least two orders of magnitude less than a volume of commercially available, pectorally implantable pulse generator, such as traditional pacemakers, cardio-defibrillators, etc.

In some examples, an outer surface of the housing of the microstimulator is electrically nonconductive such that even direct contact against the target nerve does not electrically couple circuitry within the microstimulator relative to the target nerve. Instead, such electrical coupling is implemented via an electrode structure extending outwardly from the housing of the microstimulator. However, in some examples, at least one electrically conductive element is present on the outer surface of the housing of the microstimulator such that direct contact against the target nerve does at least partially electrically couple the circuitry within the microstimulator relative to the target nerve.

In some examples, the microstimulator is implanted via nonvascular techniques and/or implanted in a subcutaneous location which is also extravascular, i.e. not within the vasculature (e.g. veins, arteries), cardiac structures, etc. In some examples, the microstimulator is implanted in a head/neck region, which is non-pectoral and as such also is a non-cardiac implantation.

These examples, and additional examples, are described in more detail in association with at least FIGS. 1-27.

FIG. 1 is diagram schematically representing a patient environment 20 including a patient 22 having a microstimulation therapy device 32 implanted within a head/neck region 24 of the patient, according to one example of the present disclosure. As shown in FIG. 1, in some examples, therapy device 32 is implanted subcutaneously in proximity to a target nerve 30. Stimulation of the target nerve 30 via therapy device 32 causes contraction of at least some muscles innervated via the target nerve 30. In some examples, the target nerve 30 and associated muscle(s) are associated with maintaining and/or restoring patency of the upper airway 36. Various aspects regarding the implantation and deployment of microstimulation therapy device 32 are described in association with at least FIGS. 2-25.

FIG. 2 is a diagram of a patient environment 50 in the head/neck region 24 (FIG. 1), according to one example of the present disclosure. As shown in FIG. 2, in some examples therapy device 32 (e.g. a microstimulator device) is sized and/or shaped to be fully implanted within a subcutaneous environment 74 below at least the skin 70 through a single incision 72. Accordingly, FIG. 2 at least partially illustrates and represents the result of a minimally invasive implantation of therapy device 32 via a percutaneous pathway, non-vascular pathway, or analogous technique to place therapy device 32 in proximity to target nerve 30.

This arrangement avoids several factors associated with implantation of a commercially available, pectorally implanted pulse generator and associated leads. For instance, such pectoral implantation involves more incisions, creating a pouch in the body to receive the pulse generator, tunneling a path for a lead to extend from the pulse generator to the target nerve, etc. While generally effective, such procedures involve a larger surgical field, more incisions, a long duration surgical event, etc. Moreover, because the lead will extend from the pectoral region into and through substantially the entire neck region, the lead may be subject to stresses and/or stability challenges associated with normal movements of the neck. Both the implantation and/or location of these various elements may contribute to patient comfort and long term effectiveness.

Accordingly, via at least some examples of the present disclosure, a minimally invasive implantation technique is implemented, thereby avoiding a number of challenges posed by pectoral implantation techniques of a pulse generator and associated lead(s).

In addition, in some examples, employing a minimally invasive implant procedure in a head/neck region in proximity to the target nerve to be stimulated, with the implant comprising a relatively small microstimulation therapy device locatable in proximity to the target nerve, may enable increased patient eligibility for receiving magnetic resonance imaging (MRI). For instance, in such examples, the patient may be eligible for a body coil MR scan since no components of the microstimulation therapy device would be present in the torso. This arrangement stands in sharp contrast to at least some commercially available pectorally implanted therapy devices, which may prohibit such body coil MR scans. As such, at least some examples of the present disclosure may enable the microstimulation therapy device to be eligible to labeled as conditionally acceptable for a body coil MR scan or other limited form of MR imaging.

With further reference to at least FIGS. 1-2, in some examples, such as the case of obstructive sleep apnea, the nerve(s) 30 may include (but are not limited to) the nerve(s) and muscles related to causing movement of the tongue and related musculature to restore upper airway patency. In some examples, the nerve(s) 30 may include (but are not limited to) the hypoglossal nerve and the muscles may include (but are not limited to) the genioglossus muscle.

As further shown in FIG. 2, microstimulation therapy device 32 is coupled (via coupling 62) relative to target nerve 30 within the subcutaneous environment 74. Notably, with the subcutaneous environment 74 being in the head/neck region 24, complications associated with a cardiac environment are avoided. Moreover, the microstimulation therapy device 32 is implanted in an extravascular manner, i.e. without the complications of introducing and delivering a device into and through the vasculature of the body.

In some examples, the microstimulation therapy device 32 is mechanically coupled relative to the nerve 30, thereby at least partially securing the therapy device 32 within the subcutaneous environment 74. At least some specific examples of such mechanical coupling are shown and described later in association with at least FIGS. 12 and 14A-18D.

In some examples, the microstimulation therapy device 32 is electrically coupled relative to the nerve 30, thereby at least partially electrically coupling the therapy device 32 relative to the nerve 30 within the subcutaneous environment 74. At least some specific examples of such electrical coupling are shown and described later in association with at least FIGS. 13 and 14A-18D.

In some examples, such mechanical coupling and electrical coupling may be implemented via a single element or via multiple elements, with some elements providing both mechanical and electrical coupling.

FIG. 3 is a block diagram schematically representing a therapy arrangement 80, according to one example of the present disclosure. As shown in FIG. 3, in arrangement 80, the microstimulation therapy device 32 is directly coupled relative to the nerve 30. In some examples, such coupling includes a direct mechanical coupling without a direct electrical coupling. In some examples, such coupling includes a direct mechanical coupling and a direct electrical coupling. At least some instances of the arrangement 80 are shown and described later in association with at least FIGS. 12-13 and 14A-18D.

FIG. 4 is a block diagram schematically representing a therapy arrangement 90, according to one example of the present disclosure. As shown in FIG. 4, in arrangement 90, the microstimulation therapy device 32 is not directly coupled relative to the nerve 30. In some examples, such coupling includes an indirect electrical coupling of the therapy device 32 and nerve 30. For instance, in some examples, the indirect electrical coupling includes circuitry within therapy device 32 being electrically coupled to the nerve 30 via conductive elements located at some distance from a surface of a housing of the therapy device. In some examples, such coupling includes an indirect mechanical coupling of therapy device 32 relative to nerve 30 via the therapy device mechanically engaging at least some portion of the subcutaneous environment 74 other than nerve 30. At least some instances of the arrangement 90 are shown and described later in association with at least FIGS. 12-13 and 14A-18D.

With this general arrangement of FIGS. 1-4 in mind, it will be understood that at least some implementations associated with FIGS. 5-25 provide more specific examples of various implementations and details regarding the operation and interaction of at least some aspects of a microstimulation therapy device relative to a target nerve 30.

Moreover, at least some examples of the present disclosure result in a more comfortable placement of the therapy device than commercially available injectable stimulators. In addition, at least some example therapy devices of the present disclosure are more securely fixed in place within the patient's body than a commercially available injectable stimulator, which tend to migrate within the patient's body. In another aspect, applying nerve stimulation via at least some examples of the present disclosure enhances patient comfort as compared to at least some commercially available direct muscle stimulators, which may tend to inhibit patient comfort and/or which may ineffectively engage the patient anatomy.

FIG. 5 is a block diagram schematically representing a microstimulation therapy device 100, according to one example of the present disclosure. In some examples, therapy device 100 comprises at least some of substantially the same features and attributes as the previously described microstimulation therapy devices and arrangements (32 in FIGS. 1-4).

As shown in FIG. 5, therapy device 100 includes power element 110, stimulation circuitry 112, communication element 114, and a control portion 120 having therapy manager 122. In some examples, the control portion 120 comprises at least some of substantially the same features and attributes as control portion 1700 as described in association with FIG. 25A and/or therapy manager 122 comprises at least some of substantially the same features and attributes as therapy manager 1705 as described in association with FIG. 25A (or therapy manager 1600 in FIG. 24).

In some examples, power element 110 provides power for the operation of microstimulation therapy device 100. At least some aspects of power element 110 are further described later in association with at least FIG. 6A.

In some examples, stimulation circuitry 112 can generate electrical signals deliverable through a stimulation element suitable for exciting a target nerve associated with muscles that can restore airway patency. In some examples, stimulation circuitry 112 produces at least substantially the same type and manner of stimulation signals as a commercially available implantable pulse generator, but with therapy device 100 having a substantially smaller size and/or shape as previously noted. For instance, in some examples, the therapy device 100 (including stimulator circuitry 112) has a volume at least one order of magnitude less than a volume of a commercially available implantable pulse generator (IPG) which is used for treating sleep disordered breathing and which is implanted at a pectoral location. In some examples, therapy device 100 has a volume at least two orders of magnitude less than a volume of such commercially available, pectorally implantable pulse generators.

In some examples, the signals are adapted to directly stimulate nerve 30 innervating upper-airway-related muscles. In some examples, such as the case of obstructive sleep apnea, the nerves 30 may include (but are not limited to) the nerve 30 and associated muscles responsible for causing movement of the tongue and related musculature to restore airway patency. In some examples, the nerves 76 may include (but are not limited to) the hypoglossal nerve and the muscles may include (but are not limited to) the genioglossus muscle.

With further reference to FIG. 5, in some examples communication element 114 enables at least some of the components of microstimulation therapy device 100 to communicate with devices, components, modules, etc. which are external to therapy device 100, whether such devices, components, modules, etc. are located elsewhere within the patient's body and/or located external to the patient's body. At least some aspects of the communication element 114 are further described later in association with at least FIG. 7.

In some examples, a therapy manager 122 comprises part of or is incorporated within the therapy device 100, such as being part of control portion 120. As such, therapy manager 122 is "on board" the therapy device 100. In some examples, a therapy manager is external to the therapy device 100 but is at least intermittently coupled to and/or in communication with the on-board therapy manager 122. In some examples, therapy manager 122 implements sleep disordered breathing (SDB) stimulation therapy but, as part of control portion 120, is also responsible for managing at least some general operations of therapy device 100.

FIG. 6A is a block diagram schematically representing the power element 110, according to one example of the present disclosure. As represented in FIG. 6A, in some examples power element 110 may be implemented via at least one of various power modalities such as a rechargeable modality 140, a storage modality 142, and/or an energy harvesting modality 144.

In some examples, the rechargeable modality 140 employs a handheld battery-operated charger external to the patient's body. On a periodic basis, the charger is placed in close proximity to the implanted microstimulation therapy device 100 to apply a fast charging protocol to ensure the therapy device 32 has sufficient power for implementing the therapy overnight. In some examples, the periodic basis is daily, weekly, or monthly.

In some examples, the rechargeable modality 140 includes an inductive element (e.g. antenna) within or associated with the microstimulation therapy device 100 and via a magnetic alignment of an antenna within the handheld charger, energy is transferred from the charger to the power element 110 within the therapy device 100. In some examples, the rechargeable modality 140 employs piezoelectric transducer(s) associated with the power element 110 to affect an ultrasonic energy transfer from the handheld charger to the power element 110 within the therapy device 100.

In some examples, the rechargeable modality 140 involves generally continuous charging in which an object in the patient's sleep environment (such as a pillow, bed, garment, etc.) includes a power source/element having an antenna to implement energy transfer to the power element 110 within the therapy device 100. In some examples, the power element 110 includes multiple antennas, each oriented in a different direction or position, and the external object (e.g. pillow, bed, etc.) includes multiple antennas oriented in different directions or positions, thereby reducing alignment sensitivity of the charging elements. In one aspect, this form of generally continuous charging is sometimes referred to as an automatic charging mode.

In some examples, the power element 110 includes a rectenna, which is a form of antenna that receives electromagnetic waves (e.g. radiofrequency waves) applied via an external device and converts those waves into direct current electricity for use by the therapy device 110.

It will be understood that in at least some of the various examples of the rechargeable modality 140, the power element 110 includes at least some short-term energy storage capability sufficient to enable stimulation therapy for at least one treatment period (e.g. a daily sleep period).

As further shown in FIG. 6A, in some examples the power element 110 comprises a storage modality 142. In some examples, the energy storage modality 142 is implemented via a long term rechargeable battery, such as but not limited to, a Lithium-Ion battery having high energy density. In some examples, the energy storage modality 142 is implemented via a supercapacitor, which provides a high charge rate and low mass, enabling a fast charging protocol of rechargeable modality 140.

As further shown in FIG. 6A, in some examples power element 110 comprises an energy harvesting modality 144. In some examples, the energy harvesting modality 144 is implemented via a thermopile-based energy harvester. In some examples, the energy harvesting modality 144 is implemented via a piezoelectric motion/deflection technique. In some instances, the energy harvesting modality 144 may enable the power element 110 to be referred to as an on-board power source (e.g. on-board power generation element), thus freeing the therapy device 100 from having to be recharged via sources external to the body via rechargeable modality 140. Accordingly, in some examples, the energy harvesting modality 144 may sometimes be referred to as a non-rechargeable modality because instead of recharging a depleted power element, new power is generated (e.g. energy harvesting) on-board the stimulator. Stated differently, via energy harvesting modality 144, therapy device 100 may operate without involving any external charging.

In some examples, the therapy device 100 may combine various aspects of the different modalities 140, 142, 144.

Via at least some of the examples of the present disclosure, expensive recharging of a power element 110 of a therapy device is at least minimized or avoided and/or typical patient non-compliance with recharging is at least minimized or avoided. Moreover, in some examples, some of the more bulky components associated with traditional recharging schemes may be minimized and/or avoided, thereby facilitating a minimally invasive implantation and/or minimal profile within the subcutaneous environment (which in turn enables direct placement in close proximity to a target nerve).

FIG. 6B is a block diagram schematically representing a power element arrangement 150, according to one example of the present disclosure. In some examples, power element arrangement 150 provides one example implementation of power element 110 and at least energy harvesting modality 144 in FIG. 6A. As shown in FIG. 6B, in some examples the power element arrangement 150 comprises a power element 152, which includes an energy harvesting element 154, mass 160, and energy storage element 162.

In some examples, the energy harvesting element 154 comprises a mechanical energy harvesting element. In some examples, the energy harvesting element 154 comprises a piezoelectric capacitor element 156 while in some examples, the energy harvesting element 154 comprises a microelectromechanical system (MEMS) capacitor element 158. In some examples, the MEMS capacitor element 158 comprises a MEMS electret capacitor. In some examples, the energy harvesting element 154 comprises an element other than piezoelectric capacitor and/or MEMS capacitor to harvest mechanical energy.

In some examples, the energy harvesting element 154 is associated with, is operably coupled to, and/or comprises mass 160. In some such examples, one side of the energy harvesting element 154 (e.g. piezoelectric capacitor or MEMS capacitor) is directly mechanical coupled to a stimulator (to provide power), while the other side of the energy harvesting element 154 is directly mechanically coupled to mass 160. Via such arrangement, mechanical vibrations, mechanical stress, and/or mechanical strain is converted via the energy harvesting element 154 (in association with mass 160) into electrical energy which is then transferred to the stimulator and/or stored in energy storage element 162, as shown in FIG. 6B.

In some examples, energy storage element 162 comprises a battery 164, a capacitor 166, and/or other storage modality 168.

The power element 152 comprises is implantable (157B) within a patient's body, at least below skin 157A. In some examples, the power element 152 may be at least partially contained within or otherwise incorporated with another implantable component, such as a housing of a stimulator or therapy device.

In some examples, the power element arrangement 150 comprises components external (157C) to skin 157C, and selectively operably coupled relative to the implantable power element 152. In some examples, the external components may comprise an external power element 170 which provides a supplemental or alternate source of power or energy to implantable components. In some examples, the external power element 170 comprises a battery 172 (which may be permanent or rechargeable), a line voltage 174, and/or other power source 176. In some instances, a control portion or a patient may select the stimulator (100, 200 in FIGS. 5, 8) to receive power from external power element 170 prior to a treatment period (e.g. sleep period) if recent energy harvesting has been insufficient to provide sufficient energy for an upcoming treatment period.

In some examples, external components associated with power element arrangement 150 may include a coupling element 180 to facilitate operable coupling of external power element 170 relative to the implantable components, e.g. power element 152. In general terms, the coupling element 180 can take a wide variety of forms, which may indirectly couple the external power element 170 through tissue to the implantable power element 152. In some examples, the coupling element 180 comprises an ultrasonic transducer 182 while in some examples, the coupling element 180 comprises other forms 184 of indirect coupling.

FIG. 6C is a side plan view schematically representing a nerve stimulation system 2600 for treating sleep disordered breathing (SDB), such as obstructive sleep apnea, according to one example of the present disclosure. As shown in FIG. 6C, in some examples system 2600 may provide therapy to a patient 26002 reclined on a support 2604. The patient support 2604 may comprise a bed 26005 and/or a headrest structure 2006 (e.g., pillow, neck support, etc). In some examples, the patient support 2604 houses at least power source 2600. In some examples, the patient support 2604 also houses and/or provides radiofrequency transmission coils 2620.

It will be understood that patient support 2604 is not strictly limited to a bed and/or pillow, but extends to other configurations in which the patient 2602 can remain stationary for an extended period of time.

As further illustrated in FIG. 6C, system 2600 includes a microstimulator 2635 which is implanted within the patient's body. In some examples, the microstimulator 2035 is implanted in the patient's head-neck region. In one aspect, FIG. 6C also depicts microstimulator 2635 in block diagram form (labeled as 2610). In some examples, microstimulator 2635 comprises any one of the stimulators (e.g. at least 100, 200 in FIG. 5, 8) and associated electrodes, cuffs, housings, flanges, etc. in any of the various forms as described throughout the examples of the present disclosure in association with FIGS. 1-27.

Referring again to FIG. 6C, in some examples system 2600 also includes at least one sensor arrangement 2680. The sensor arrangement 2680 may comprise a single sensor or multiple sensors as implemented via at least one of the sensors (e.g. types of sensors, sensing arrangements, etc.) as previously described in association with at least sensors 210 in FIG. 9A, 250 in FIG. 9B, and/or 300 in FIG. 10. As further described later, sensed information obtained via the sensor arrangement 2680 may be communicated to the implanted microstimulator 2635 via at least a sensor information transmission function 2670 of the charging station 2650.

As just one example of the many different forms and modes of sensing via sensor arrangement, FIG. 6C schematically represents at least some aspects of external sensing. In some examples, such sensing may be suitable for detection of an apnea and for triggering application of the stimulation signal synchronous with respiration, such as with inspiration. However, it will be understood that the sensed information may be used for other purposes and does not necessitate closed loop operation of the system 2600. Accordingly, in some examples, at least some sensing is provided via an externally securable belt 2630 including a wearable, external sensor 2631. In some examples, signals sensed at sensor 2631 are transmitted wirelessly to a control portion (e.g. 1700 in FIG. 25B) for use in apnea detection and treatment, etc. In some examples, the control portion 1700 is associated with, incorporated with, and/or coupled to power element 2622.

In some examples, sensing is provided via a sensor 640 secured on an external surface of a chest via a patch or even implanted subcutaneously. Sensor 2640 communicates wirelessly with power element 2622 and/or control portion 1700. In some embodiments, belt 2630 or the other sensor 2640 includes an accelerometer or piezoelectric transducer for detecting body motion/position and/or many other types of physiologic information, with such sensed information also being used within system 2600.

In some examples, system 2600 comprises a charging station 2650 to supply power to a power element (e.g. at least 140 in FIG. 6A, 152 in FIG. 6B, 110 in FIGS. 5, 8) 6B in microstimulator 2635. In some examples, system 2600 transmits the power to the implantable microstimulator 2635 via coils 2620. It is also understood that in some examples, coils 2620 also may be used to transmit and/or receive control information relative to the microstimulator 2635. In some examples, coils 2620 may be used to transmit and/or receive sensor information relative to the microstimulator 2635.

In some examples, a power element (e.g. 110 in FIGS. 5, 6A, 8) associated with the microstimulator 2635 comprises an implantable, re-chargeable first portion and an external second portion to selectively re-charge the first portion. The second portion is external to the patient. The first portion may comprise a power element contained within or otherwise coupled to implantable microstimulator 2635. In some examples, the second portion is implemented via at least some of the features and attributes of charging station 2650 whether alone or in association with patient support 2604, 2606, coils 2620, etc.

In some examples, charging station 2650 comprises an inductive charging arrangement 2652 by which power is transmitted to rechargeable power element in microstimulator 2635 via coils 2620 according to a general induction element(s) 2654 or a highly resonant induction element(s) 2656.

In some examples, charging station 2650 comprises a radiofrequency (RF) charging arrangement 2660 by which power is transmitted to rechargeable power element in microstimulator 2635 according to an RF rectification element(s) 2662 or a low power microwave element(s) 2664.

As previously noted, in some examples the charging station 2650 includes a sensor information transmission function 2670 by which sensed information may be transmitted to the microstimulator 2635. In some examples, the sensor information transmission function 2670 transmits the sensed information as part of a re-charging signal transmitted in association with the re-charging functions of charging station 2650.

In some examples, at least some aspects of the charging station 2650 may provide one example implementation of the external power element 170 in the arrangement of FIG. 6B.

In some examples, it will be understood that at least a portion and/or at least some functions of the charging station may be implemented via a handheld device.

FIG. 7 is a block diagram schematically representing communication element 112, according to one example of the present disclosure. As represented in FIG. 7, in some examples communication element 112 may be implemented via at least one of various communication modalities such as an external communication modality 190, an inductive communication modality 192, and/or a radiofrequency communication modality 194. It will be understood that in some examples these various modalities are not mutually exclusive.

In some examples, communication element 112 is implemented via an external communication modality 190 in which a device external to the patient communicates information to, and receives information from, the therapy device 100. In some examples, this modality enables the external device to configure various therapy parameters by programming and/or adjusting parameters of the therapy manager 122 and/or control portion 120 of therapy device 100.

In some examples, the inductive communication modality 192 performs communication via a set of coils separate from, and different from, any coils implemented as part of power element 110 (e.g. FIGS. 5-6). In some examples, the inductive communication modality 192 performs communication via at least some coils which are common with at least some coils implemented as part of one of the modalities of power element 110 (FIGS. 5-6).

In some examples, the radiofrequency modality 194 shown in FIG. 7 enables reducing power requirements during communication via an asymmetric protocol in which transmissions from the implanted therapy device 100 to the external device uses a lower data rate.

In some examples, the radiofrequency modality 194 enables reduced power usage via wakeup rate optimization. In some examples, an increase wakeup rate is used to decrease communication latency. In some examples, application of an external magnet is used to increase wakeup rate. In some examples, prediction of onset of sleep is used to increase wakeup rate. In some examples, these arrangements are employed via an external power source with a radiofrequency (RF) link.

Accordingly, it will be understood that in some examples, at least some of these aspects of communication element 112 enhance and/or may define at least a portion of power element 110. Similarly, in some examples and as noted elsewhere throughout at least some examples of the present disclosure, power element 110 may define at least a portion of communication element 112.

Figure 8:
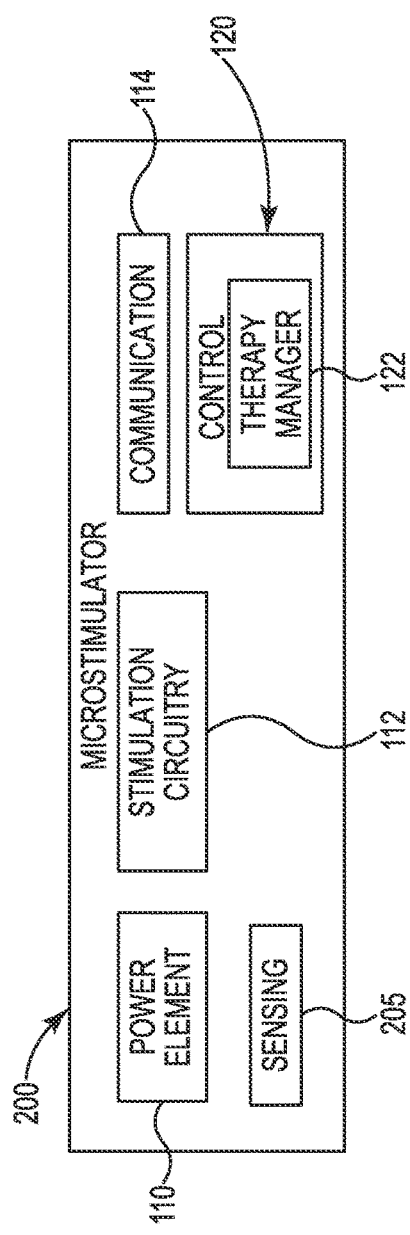
FIG. 8 is a diagram schematically representing a microstimulator of a microstimulation therapy device including a sensing function, according to one example of the present disclosure.

FIG. 8 is a block diagram schematically representing components of a microstimulation therapy device 200, according to one example of the present disclosure. As shown in FIG. 8, microstimulation therapy device 200 includes power element 110, stimulation circuitry 112, communication element 114, and a control portion 120 having therapy manager 122. In some examples, microstimulation therapy device 200 includes at least some of substantially the same features and attributes as microstimulation therapy device 100 as previously described in association with at least FIG. 5, except for microstimulation therapy device 200 further including a sensing function 205. In some examples, sensing function 205 receives sensed information for further use by therapy manager 122 and/or control portion 120 to evaluate and/or perform therapy. As such, in some examples, sensing function 205 provides feedback to enable operation of therapy device 200 in a closed loop system. One such closed loop function 1630 is described later in association with at least FIG. 24, while other aspects associated with closed loop functioning are described throughout at least some examples of the present disclosure.

In some examples, sensing function 205 is implemented via a sensor (210 in FIG. 9A; 250 in FIG. 9B; 300 in FIG. 10) forming part of microstimulation therapy device 200. However, in some examples, a sensor (210 in FIG. 9A; 250 in FIG. 9B; 300 in FIG. 10) may be separate from, and independent of a therapy device (FIG. 8), according to one example of the present disclosure. In some examples, while separate from and independent of therapy device 200, a sensor (210 in FIG. 9A; 250 in FIG. 9B; 300 in FIG. 10) is dedicated to providing sensed information to therapy device 200.

In some examples, a sensor (210 in FIG. 9A; 250 in FIG. 9B; 300 in FIG. 10) is not dedicated to providing sensed information to microstimulation therapy device 200. As such sensor 210/250/300 may be part of a system which is independent of therapy device 200 or sensor 210/250/300 may be a standalone sensor not associated with any other system or device. For instance, in some examples, a sensor (210, 250, and 300) comprises a portion of a cardiac device.

In either case, further details regarding at least some examples of such sensors are described later in association with at least FIGS. 9-10.

With further reference to FIG. 8, the sensing function 205 receives and tracks signals from various physiologic sensors in order to determine respiratory information, sleep quality information, sleep disordered breathing (SDB) information, cardiac information, etc. This information may be received from either a single sensor or any multiple of sensors, or combination of various physiologic sensors which may provide a more reliable and accurate signal. In some examples, sensing function 205 receives this information from sensor(s) 210, 250 300, as later described in association with at least FIGS. 9-10.

FIG. 9A is a block diagram schematically representing a sensor 210, according to one example of the present disclosure. In some examples, sensor 210 corresponds to a sensor external to microstimulation therapy device 200 which cooperates with sensing function 205 of microstimulation therapy device 200 in FIG. 8 and/or corresponds to a sensor incorporated within the microstimulation therapy device 200 which at least partially implements the sensing function 205 in FIG. 8, as previously described or later described in the examples of the present disclosure.

In some examples, sensor 210 is an implantable sensor implanted within a patient's body separately from microstimulation therapy device 200, as represented by 226 in FIG. 9A. In some examples, an implantable sensor forms part of another component implanted within the patient's body, such as on-board the microstimulation therapy device 200 in FIG. 8, and as such is represented by 220 in FIG. 9. In such examples, the on-board sensor 220 may form part of the housing of the microstimulation therapy device 200 and therefore may be exposed to the internal environment of the patient. On the other hand, in such examples, the on-board sensor 220 may be housed internally within the microstimulation therapy device 200 and be isolated from the internal environment of the patient. While a fuller discussion of sensor types 300 is reserved until a later discussion of FIG. 10, it will be noted that an accelerometer (e.g. 306 in FIG. 10) is one example of an implantable sensor, which may be internally housed within a microstimulation device as an on-board sensor 220.

In some examples, implantable sensor 226 may comprise stand-alone implantable sensors distributed throughout the patient's body and which communicate wirelessly to a microstimulation therapy device 200 or to an external device that integrates the sensed data. For instance, one stand-alone implantable sensor may comprise an oxygen sensor.

With further reference to FIG. 9A, in some examples sensor 210 comprises an external sensor 222 that remains external to a patient's body. The external sensor 222 may be a wearable sensor 230 or an environment sensor 232, which is part of the patient's environment and which senses information from the patient and/or regarding the environment in which the patient is present. In some examples, a wearable sensor 230 may be used to sense heart rate variability such that the wearable sensor 230 need not be part of an implantable microstimulation therapy device 200 or external therapy device. Rather, one may simply add the wearable sensor 230 at a later time to monitor parameters associated with a therapy performed to alleviate sleep disordered breathing.

In some examples, a wearable sensor 230 may comprise a commercially available wearable sensor which includes an array of sensors for measuring heart rate (e.g. LED, optical sensor), sleep quality/motion (e.g. 3D accelerometer), ambient light, etc. In some instances, the wearable sensor 230 includes a touchscreen display to facilitate tracking and monitoring of the sensed conditions. In some instances, the wearable sensor 230 includes a wireless communication tool for communicating with a dongle, mobile device, etc. via a wireless communication protocol (e.g. Bluetooth, NFC, etc.). In one instance, such a wearable sensor 230 is available from FitBit, Inc. of San Francisco, Calif. In some examples, such a system may include a single sensor or array of sensors which provide respiratory information, cardiac information, sleep quality information, sleep disordered breathing (SDB) information, and/or other information. In some examples, this information may be coordinated with information sensed or determined via the microstimulation therapy device 200. In some examples, the therapy manager 122 may include a sensor profile manager to coordinate information sensed via the wearable sensor 230.

In some examples, information from external sensors 222 can be coordinated with information from implantable sensors 220, 226.

In some examples, external sensor 222 comprises an integrated external sensing system for tracking sleep quality, heart rate, breathing rhythm, movement, sleep stages, snoring, and sleep environment (e.g., noise level and light). One example system comprises the Beddit® system available from www.beddit.com. In some examples, such a system may provide respiratory information, cardiac information, sleep quality information, sleep disordered breathing (SDB) information, and/or other information. In some examples, this information may be coordinated with information sensed or determined via the microstimulation therapy device 200. In some examples, the therapy manager 122 may include a sensor profile manager to coordinate information sensed via the external sensor 220.

In some examples, an external sensor(s) 222 may comprise clinically available diagnostic equipment such as ECG sensors, a blood pressure cuff, oxygen sensor, etc.

In some instances, the environment sensor 232 shown in FIG. 9 comprises a non-contact sensor 234, which does not make contact with the patient. In one instance, non-contact sensor 234 comprises at least some of substantially the same features and attributes as the non-contact sensor paradigm described in Heneghan et al. U.S. Pat. No. 5,562,526, which may be used by microstimulator device 200 to provide respiratory information, cardiac information, sleep quality information, sleep disordered breathing (SDB) information, and/or other information. In one instance, one such system is available from Resmed Corporation of San Diego, Calif.

Figure 10:
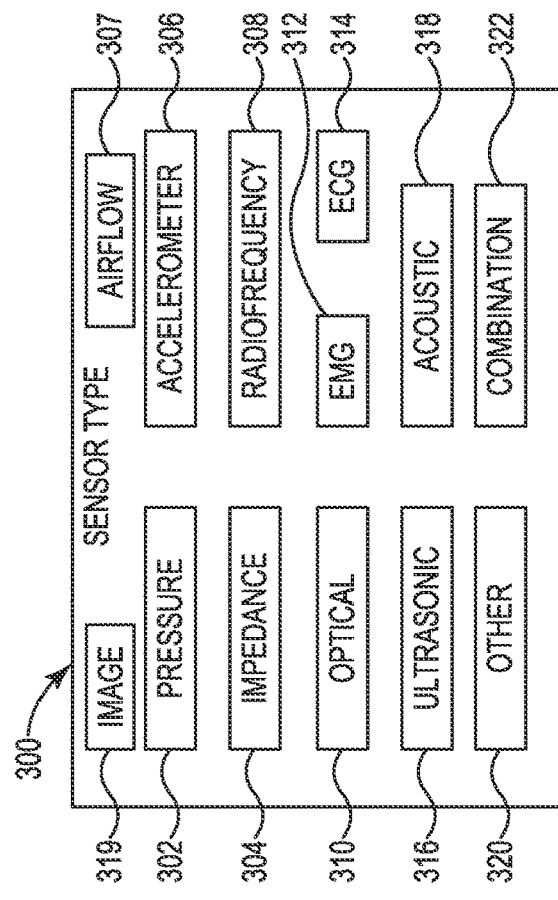
FIG. 10 is a block diagram schematically representing sensor types, according to one example of the present disclosure.

In some instances, the non-contact sensor 234 incorporates or cooperates with one of the sensor modalities described in association with at least FIG. 10, such as but not limited to, a radiofrequency sensor 308. The signal produced by sensing via the radiofrequency sensor 308 may be processed to detect patient motion/activity, breathing (e.g. respiratory rate), heart rate, and/or a sleep stage of the patient.

In some examples, sensor 210 may comprise a sensor providing a combination sensor or combination sensor array, which combines at least some aspects of the various implantable sensors and external sensors.

In some examples, sensor 210 comprises an electrode associated with the microstimulation therapy device (100 in FIG. 5; 200 in FIG. 8) and as later further described in association with at least FIGS. 14A-18B, 19A-20B, 21A-23B, in which a stimulation signal generated via the stimulation circuitry of one of the microstimulation therapy devices 100, 200 is applied to a target nerve via such an electrode. In some instances, such electrodes may sometimes also be used as a sensor, such as but not limited to, sensing a bio-impedance of the patient to obtain respiratory information, cardiac information, sleep quality information, sleep disordered breathing (SDB) information, etc.

In some examples, sensor 210 includes and/or utilizes inductive coupling to effectuate communication between sensor 210 and at least some components (e.g. communication element 114 in FIG. 8) of the microstimulation therapy device 200 (FIG. 8).

Figure 9B:
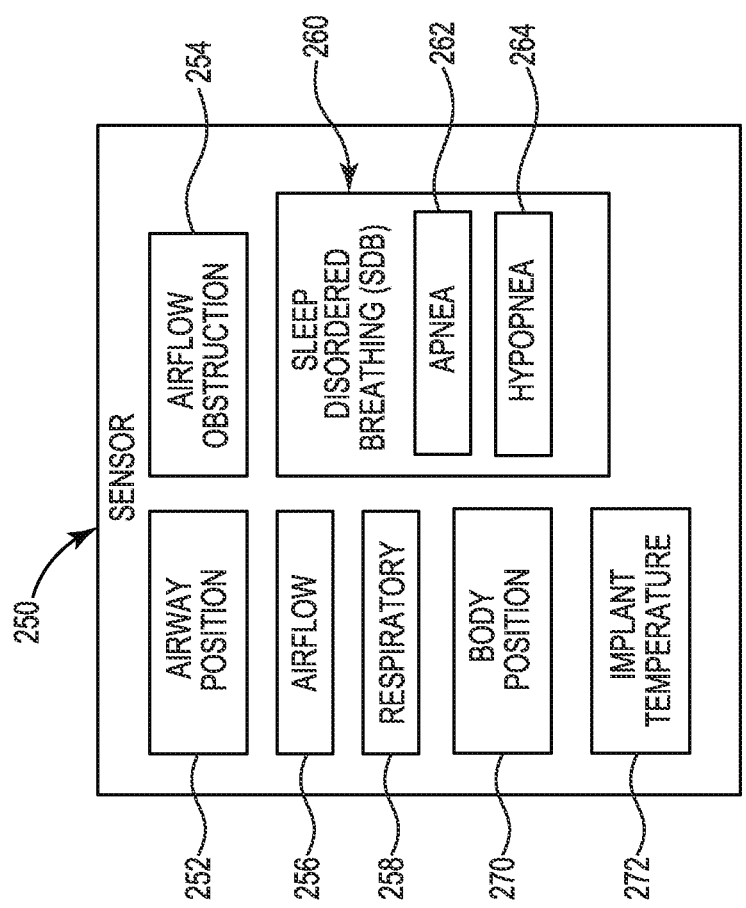
FIG. 9B is a block diagram schematically representing different sensing arrangements, according to one example of the present disclosure.

FIG. 9B is a block diagram schematically representing a sensor type 250, according to one example of the present disclosure. In some examples, at least some of the sensing arrangements 252-272 in FIG. 9B may be implemented via at least some of the sensor types 220-234 in FIG. 9A and/or sensor types 302-322 in FIG. 10. As shown in FIG. 9B, in some examples one sensor type comprises an airway position sensing arrangement 252 provide sensed information regarding an airway position while airflow obstruction sensing arrangement 254 provides sensed information regarding airflow obstructions. In some examples, airflow sensing arrangement 256 provides sensed general airflow information. As further shown in FIG. 9B, in some examples respiratory sensing arrangement 258 provides general and/or specific sensed respiratory information while in some examples, sleep disordered breathing (SDB) sensing arrangement 260 provides sensed information regarding at least sleep disordered breathing (SDB) events, such as but not limited to apneas 262 and/or hypopneas 264. In some examples, body position sensing arrangement 270 provides sensed information related to at least body position, which may involve posture, motion, activity, body orientation, etc. In some examples, implant temperature sensing arrangement 272 provides sensed information regarding at least a temperature of an implant. In some examples, such sensed implant temperature information facilitates recharging modalities and functionalities.

In some examples, sensed information may be obtained via a combination of at least some of the various sensing arrangements 252-272 in FIG. 9B.

FIG. 10 is a block diagram schematically representing a sensor type 300 according to one example of the present disclosure. In some examples, sensor type 300 corresponds to a sensor (e.g., 210 in FIG. 9) and/or a sensing function (205 in FIG. 8), as previously described or later described in the examples of the present disclosure.

As shown in FIG. 10, sensor type 300 comprises various types of sensor modalities 302-320, any one of which may be used for determining, obtaining, and/or monitoring respiratory information, cardiac information, sleep quality information, sleep disordered breathing-related information, and/or other information related to providing patient therapy.

As shown in FIG. 10, in some examples sensor type 300 comprises the modalities of pressure 302, impedance 304, accelerometer 306, airflow 307, radiofrequency (RF) 308, optical 310, electromyography (EMG) 312, electrocardiography (ECG) 314, ultrasonic 316, acoustic 318, image 319, and/or other 320. In some examples, sensor type 300 comprises a combination 322 of at least some of the various sensor modalities 302-320.

It will be understood that, depending upon the attribute being sensed, in some instances a given sensor modality identified within FIG. 10 may include multiple sensing components while in some instances, a given sensor modality may include a single sensing component. Moreover, in some instances, a given sensor modality identified within FIG. 10 may include power circuitry, monitoring circuitry, and/or communication circuitry. However, in some instances a given sensor modality in FIG. 10 may omit some power, monitoring, and/or communication circuitry but may cooperate with such monitoring or communication circuitry located elsewhere.

In some examples, a pressure sensor 302 may sense pressure associated with respiration and can be implemented as an external sensor 222 (FIG. 9) and/or an implantable sensor 226 (FIG. 9). In some instances, such pressures may include an extrapleural pressure, intrapleural pressures, etc. For example, one pressure sensor 302 may comprise an implantable respiratory sensor, such as that disclosed in Ni et al. U.S. Patent Publication 2011-0152706, published on Jun. 23, 2011, titled METHOD AND APPARATUS FOR SENSING RESPIRATORY PRESSURE IN AN IMPLANTABLE STIMULATION SYSTEM.

In some instances, pressure sensor 302 may include a respiratory pressure belt worn about the patient's body.

In some examples, a pressure sensor 302 can sense sound and/or pressure waves at a different frequency than occur for respiration (e.g. inspiration, exhalation, etc.). In some instances, this data can be used to track cardiac parameters of patients via a respiratory rate and/or a heart rate. In some instances, such data can be used to approximate electrocardiogram information, such as a QRS complex. In some instances, the detected heart rate is used to identify a relative degree of organized heart rate variability, in which organized heart rate variability may enable detecting apneas or other sleep disordered breathing events, which may enable evaluating efficacy of sleep disordered breathing.

In some examples, pressure sensor 302 comprises piezoelectric element(s) and may be used to detect sleep disordered breathing (SDB) events (e.g. apnea-hypopnea events), to detect onset of inspiration, and/or detection of an inspiratory rate, etc.

As shown in FIG. 10, in some examples one sensor modality includes air flow sensor 307, which can be used to sense respiratory information, sleep disordered breathing-related information, sleep quality information, etc. In some instances, air flow sensor 307 detects a rate or volume of upper respiratory air flow.

As shown in FIG. 10, in some examples one sensor modality includes impedance sensor 304. In some examples, impedance sensor 304 may be implemented in some examples via various sensors distributed about the upper body for measuring a bio-impedance signal, whether the sensors are internal and/or external. In some examples, the impedance sensor 304 senses an impedance indicative of an upper airway collapse.

In some instances, the sensors are positioned about a chest region to measure a trans-thoracic bio-impedance to produce at least a respiratory waveform.

In some instances, at least one sensor involved in measuring bio-impedance can form part of a pulse generator, whether implantable or external. In some instances, at least one sensor involved in measuring bio-impedance can form part of a stimulation element and/or stimulation circuitry. In some instances, at least one sensor forms part of a lead extending between a pulse generator and a stimulation element.

In some examples, impedance sensor 304 is implemented via a pair of elements on opposite sides of an upper airway. Some example implementations of such an arrangement are further described later in association with at least FIG. 11.

In some examples, impedance sensor 304 may take the form of electrical components not used in a microstimulation therapy device 200. For instance, some patients may already have a cardiac therapy device (e.g. pacemaker, defibrillator, etc.) implanted within their bodies, and therefore have some cardiac leads implanted within their body. Accordingly, the cardiac leads may function together or in cooperation with other resistive/electrical elements to provide impedance sensing.

In some examples, whether internal and/or external, impedance sensor(s) 304 may be used to sense an electrocardiogram (ECG) signal.

In some examples, impedance sensor 304 is used to detect sleep disordered breathing (SDB) events (e.g. apnea-hypopnea events), to detect onset of inspiration, and/or detection of an inspiratory rate, etc.

As shown in FIG. 10, in some examples one sensor modality includes an accelerometer 306. In some instances, accelerometer 306 is generally incorporated within or associated with microstimulation therapy device 200. For instance, in some examples of a therapy device 200, a housing (e.g. can) contains numerous components such as control circuitry, stimulation, and also may contain an accelerometer 306 within the housing. However, in some examples, the accelerometer 306 may be separate from, and independent of, the microstimulation therapy device 200. In some examples, accelerometer 306 can enable sensing body position, body posture, and/or body activity/motion regarding the patient, which may be indicative of behaviors from which sleep quality information or sleep disordered breathing (SDB) information may be determined. In some instances, body posture/position is sensed via at least the accelerometer 306 and is used to detect start of sleep.

For instance, as further addressed in association with at least FIG. 24, sleep position (e.g. left side, right side, supine, etc.) may be used to determine the effectiveness of SDB therapy according to sleep position, and in some instances, the SDB therapy may be automatically adjusted based on the orientation (i.e. sleep position) of the patient. In some instances, this information regarding sleep position may be communicated to the patient during a sleep period in order to induce the patient to change their sleep position into one more conducive to efficacious therapy. In some examples, the communication may occur by an audible or vibratory alarm implemented via wireless communication to a patient remote or via direct muscle stimulation via wireless communication to a wearable muscle stimulation device.

Among other uses, the information obtained via the accelerometer 306 may be employed by a clinician to adjust stimulation therapy and/or employed by a therapy device (and/or manager) to automatically adjust stimulation therapy to cause a decrease in the moving average of the sleep apnea index (e.g. AHI). Moreover, as previously mentioned this information may be used to communicate to the patient via audio or non-audio techniques to change their sleep position to a position (e.g. left side) more amenable to regular respiration.

In some examples, accelerometer 306 enables acoustic detection of cardiac information, such as heart rate via motion of tissue in the head/neck region, similar to ballistocardiogram and/or seismocardiogram techniques. In some examples, measuring the heart rate includes sensing heart rate variability. In some examples, accelerometer 306 can sense respiratory information, such as but not limited to, a respiratory rate. In some examples, whether sensed via an accelerometer 306 alone or in conjunction with other sensors, one can track cardiac information and respiratory information simultaneously by exploiting the behavior of the cardiac signal in which a cardiac waveform can vary with respiration.

In some examples, accelerometer 306 enables detection of sleep/awake via the sensing of motion, position, posture and/or activity of the patient, along with other parameters determinable via the accelerometer 406. In some instance, this information may be used to implement automatic control of stimulation therapy to enhance therapeutic efficacy and/or reduce power requirements.

In some examples, accelerometer 306 is used to detect sleep disordered breathing (SDB) events (e.g. apnea-hypopnea events), to detect onset of inspiration, and/or detection of an inspiratory rate, etc.

In some examples, the accelerometer 306 comprises an external sensor 222 (FIG. 9). In some instances, when embodied as an external sensor, the accelerometer 306 may comprise a wearable sensor, such as an accelerometer incorporated into a band or belt worn about a portion of the body (e.g. wrist, chest, arm, leg, torso, etc.).

In some examples, the accelerometer 306 may be used to detect sleep disordered breathing events during the sleep period and may be used continuously to detect arrhythmias.

In some examples, radiofrequency sensor 308 shown in FIG. 10 enables non-contact sensing of various physiologic parameters and information, such as but not limited to respiratory information, cardiac information, motion/activity, and/or sleep quality, such as previously described regarding non-contact sensor 234 in association with at least FIG. 9. In some examples, radiofrequency sensor 308 enables non-contact sensing of other physiologic information. In some examples, radio-frequency (RF) sensor 308 determines chest motion based on Doppler principles. The sensor 308 can be located anywhere within the vicinity of the patient, such as various locations within the room (e.g. bedroom) in which the patient is sleeping. In some examples, the sensor 308 is coupled to a monitoring device to enable data transmission relative to other components of a microstimulation therapy device 200 and storage in such other components.

In some examples, one sensor modality may comprise an optical sensor 310 as shown in FIG. 10. In some instances, optical sensor 310 may be an implantable sensor 226 and/or external sensor 222 (FIG. 9). For instance, one implementation of an optical sensor 310 comprises an external optical sensor for sensing heart rate and/or oxygen saturation via pulse oximetry. In some instances, the optical sensor 310 enables measuring oxygen desaturation index (ODI). In some examples, the optical sensor 310 comprises an external sensor removably couplable on the finger of the patient.

In some examples, optical sensor 310 can be used to measure ambient light in the patient's sleep environment, thereby enabling an evaluation of the effectiveness of the patient's sleep hygiene and/or sleeping patterns.

As shown in FIG. 10, in some examples one sensor modality comprises EMG sensor 312, which records and evaluates electrical activity produced by muscles, whether the muscles are activated electrically or neurologically. In some instances, the EMG sensor 312 is used to sense respiratory information, such as but not limited to, respiratory rate, apnea events, hypopnea events, whether the apnea is obstructive or central in origin, etc. For instance, central apneas may show no respiratory EMG effort.

In some instances, the EMG sensor 312 may comprise a surface EMG sensor while, in some instances, the EMG sensor 312 may comprise an intramuscular sensor. In some instances, at least a portion of the EMG sensor 312 is implantable within the patient's body and therefore remains available for performing electromyography on a long term basis.

In some examples, one sensor modality may comprise ECG sensor 314 which produces an electrocardiogram (ECG) signal. In some instances, the ECG sensor 314 comprises a plurality of electrodes distributable about a chest region of the patient and from which the ECG signal is obtainable. In some instances, a dedicated ECG sensor(s) 314 is not employed, but other sensors such as an array of bio-impedance sensors 304 are employed to obtain an ECG signal. In some instances, a dedicated ECG sensor(s) is not employed but ECG information is derived from a respiratory waveform, which may be obtained via any one or several of the sensor modalities in sensor type 300 in FIG. 10. In some examples, ECG sensor 314 is embodied as an accelerometer 306 as previously described in association with FIGS. 9-10.

In some examples, an ECG signal obtained via ECG sensor 314 may be combined with respiratory sensing (via pressure sensor 302 or impedance sensor 304) to determine minute ventilation, as well as a rate and phase of respiration. In some examples, the ECG sensor 314 may be exploited to obtain respiratory information (e.g. at least 1660 in FIG. 24). In some examples, as noted elsewhere, ECG sensor 314 may be implemented, at least in part, as an accelerometer 306 (FIG. 10).

In some examples, ECG sensor 314 is used to detect sleep disordered breathing (SDB) events (e.g. apnea-hypopnea events), to detect onset of inspiration, and/or detection of an inspiratory rate, etc.

As shown in FIG. 10, in some examples one sensor modality includes an ultrasonic sensor 316. In some instances, ultrasonic sensor 316 is locatable in close proximity to an opening (e.g. nose, mouth) of the patient's upper airway and via ultrasonic signal detection and processing, may sense exhaled air to enable determining respiratory information, sleep quality information, sleep disordered breathing information, etc. In some instances, ultrasonic sensor 316 may comprise at least some of substantially the same features and attributes as described in association with at least Arlotto et al. PCT Published Patent Application 2015-014915 published on Feb. 5, 2015.

In some examples, acoustic sensor 318 comprises piezoelectric element(s), which sense acoustic vibration. In some implementations, such acoustic vibratory sensing may be used to detect sleep disordered breathing (SDB) events (e.g. apnea-hypopnea events), to detect onset of inspiration, and/or detection of an inspiratory rate, etc.

In some examples, acoustic sensor 318 detects snoring information, which may be used in detection, evaluation, and/or modification of sleep-related information and/or therapy parameters.

In some examples, one of the sensor types 300 (and/or sensors 200) or a combination of such sensors senses local or gross motion, such as snoring, inspiration/expiration, etc., which may be indicative to sleep quality, sleep disordered breathing events, general respiratory information, etc.

In some examples, information sensed via sensor 210 in FIG. 9 and/or via sensor types 300 in FIG. 10, such as but not limited to motion information, can be used in a training mode of the microstimulation therapy device (200 in FIG. 8) to correlate the patient's respiration with the sensed motion.

In some examples, several sensor modalities of the sensory types 300 are combined, as represented via combination identifier 322.

Figure 11:
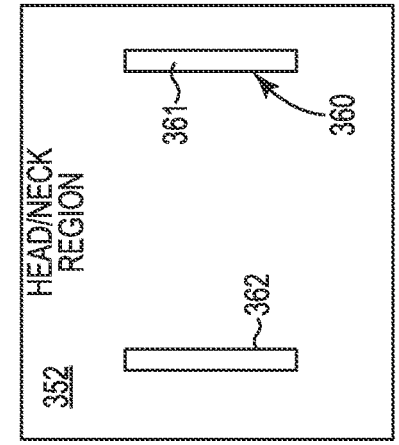
FIG. 11 is a diagram schematically representing a sensor array implanted in a head/neck region, according to one example of the present disclosure.

FIG. 11 is a diagram 350 schematically representing an impedance sensor array 360 implanted in a head/neck region 352, according to one example of the present disclosure. In some examples, impedance sensor array 360 comprises at least some of substantially the same features and attributes as impedance sensor 304 (FIG. 10). As shown in FIG. 11, sensor array 360 includes a first sensing element 361 and a second sensing element 362. In some examples, both sensing elements 361, 362 comprise some form of electrically conductive element such that a bio-impedance can be measured between the respective sensing elements 361, 362 positioned on opposite sides of an upper airway in the head/neck region 352. In some examples, the measured bio-impedance may indicate a relative degree of upper airway patency or collapse. In some examples, one or both of sensing elements 361, 362 may comprise tines to prevent migration of the respective sensing elements 361, 362.

In some examples, the sensing element 361 comprises at least a conductive element of a microstimulation therapy device, such as therapy device 200 in FIG. 8. Accordingly, the therapy device 200 itself may form part of the impedance sensor array 360. In this arrangement, in some examples, the other sensing element 362 is inserted at the opposite side of the head/neck region 352 via use of a tunneling tool.

In some examples, the sensing element 361 comprises a housing of a first microstimulation therapy device, such as therapy device 200 in FIG. 8 and the other sensing element 362 comprises a housing of a second microstimulation therapy device, which is separate from, and independent of the first microstimulation therapy device 200. In some implementations, these sensing elements 361, 362 function as an impedance sensor 304. In some implementations, the two sensing elements 361, 362 (implemented via two independent microstimulation therapy devices 200) are placed on opposite sides of the throat of the patient and communicate wirelessly with each other to sense inhalation and exhalation.

Figure 12:
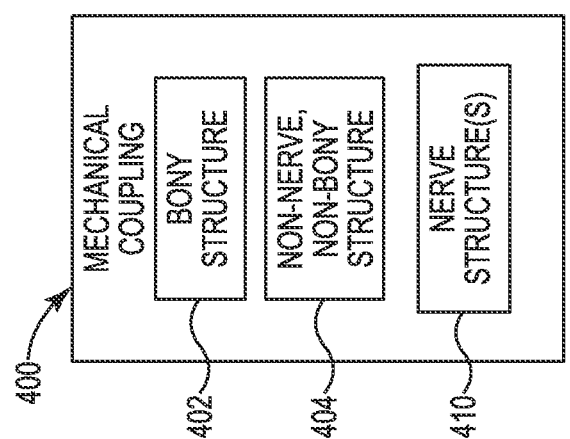
FIG. 12 is a block diagram schematically representing mechanical coupling arrangements, according to one example of the present disclosure.

FIG. 12 is a block diagram schematically representing mechanical coupling arrangements 400 for securing at least a microstimulation therapy device within a subcutaneous environment, according to one example of the present disclosure. As shown in FIG. 12, one coupling arrangement includes a bony structure coupling arrangement 402 in which at least a portion of the housing of the microstimulation therapy device (e.g. 100 in FIG. 5, 200 in FIG. 8) is secured via a fixation mechanism relative to a bony structure accessible within a subcutaneous environment. In this arrangement, a stimulation element such as a contact electrode is located at a target nerve while the housing of the microstimulation therapy device (e.g. 100, 200) is spaced apart from the target nerve stimulation site. In some instances, the housing may be considered to be located remotely from the target nerve site.

For instance, in some examples, the bony structure may comprise the mandible. In some instances, the housing of the therapy device 100, 200 is fixed via screws or other fastening mechanism(s). In some instances, fixation occurs at an inferior portion of the mandible and may potentially involve bone removal to facilitate the fixation. In some instances, fixation occurs at inner portion of the mandible but without involving bone removal.

In some examples, the housing of the microstimulation therapy device 100, 200 can be placed behind the ear, or elsewhere on the cranium. In such arrangements, fixation may occur via a screw associated with the housing of the therapy device 100, 200 and/or via other fixation mechanisms.

As shown in FIG. 12, one coupling arrangement includes a non-nerve, non-bony structure coupling arrangement 404 in which at least a portion of the housing of the microstimulation therapy device 100, 200 is secured via a fixation mechanism relative to a non-bony structure accessible within a subcutaneous environment. In this arrangement, a stimulation element such as a contact electrode is located at a target nerve while the housing of the microstimulation therapy device (e.g. 100, 200) is spaced apart from the target nerve stimulation site. In some instances, the housing is located remotely from the target nerve stimulation site. In some instances, the housing of the microstimulation therapy device (e.g. 100, 200) can be placed superior to the mylohyoid, which in some instances, further involves the use of tines for mechanical fixation to prevent migration.

In some examples, a microstimulation therapy device 100, 200 secured via arrangements 402 or 404 can communicate with either an implanted generator (e.g. pectoral) or external generator module which can contain a power source accessible by the implanted microstimulation therapy device.

In some examples, a microstimulation therapy device 100, 200 secured via arrangements 402 or 404 can communicate with a sensor 210, 300, whether implanted or external. In some implementations, the sensor 210, 300 can be passively powered or can have an internal primary/rechargeable power source.

As shown in FIG. 12, one coupling arrangement includes a nerve structure coupling arrangement 410 in which at least a portion of the housing of the microstimulation therapy device 100, 200 is secured via a fixation mechanism relative to a nerve within a subcutaneous environment. In this arrangement, at least a housing of the microstimulation therapy device 100, 200 is located directly at the target nerve stimulation site. In some examples in which a stimulation element (e.g. contact electrode) extends from the housing of the microstimulation therapy device, both the microstimulation therapy device 100, 200 and stimulation element may be located in close proximity to a target stimulation site, as later shown and described in association with at least FIGS. 14A-18D.

Figure 13:
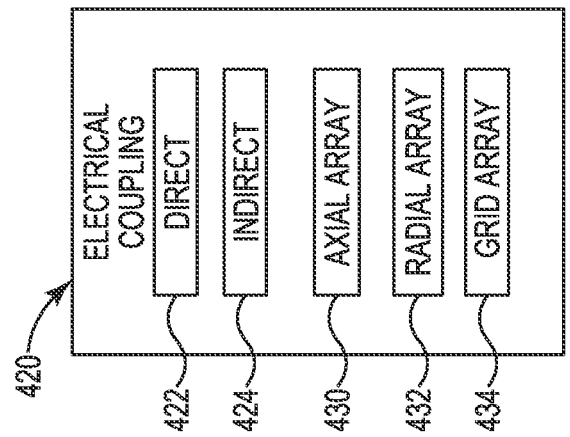
FIG. 13 is a block diagram schematically representing electrical coupling arrangements, according to one example of the present disclosure.

FIG. 13 is a block diagram schematically representing electrical coupling arrangements 422-434 for a microstimulation therapy device, according to one example of the present disclosure. In general terms, the various electrical coupling arrangements 422-434 provide a means by which stimulation pulses from the microstimulation therapy device 100, 200 are coupled to a target nerve.

As shown in FIG. 13, one coupling arrangement includes a direct coupling arrangement 422 in which a housing of the microstimulation therapy device 100, 200 includes at least one exposed electrically conductive element that directly contacts the target nerve. In one aspect, one such arrangement is further described later in association with at least FIGS. 16A-16C. In some examples, an array of such conductive elements is present on an outer surface of the housing of the microstimulation therapy device. In one aspect, one such arrangement is further described later in association with at least FIGS. 14A-14B.

As shown in FIG. 13, one coupling arrangement includes an indirect coupling arrangement 424 in which an outer surface of the housing of the microstimulation therapy device 100, 200 does not include any exposed electrically conductive elements. In one aspect, one such arrangement is further described later in association with at least FIGS. 15A-15B in which an electrode array extends outwardly from the housing of the microstimulation therapy device to establish contact with the target nerve.

As shown in FIG. 13, one coupling arrangement includes an axial array coupling arrangement 430 in which an array of electrically conductive elements is arranged to be axially aligned with a length of the target nerve. In some examples, the axial array of conductive elements is located on an outer surface of a housing of the microstimulation therapy device. In one aspect, one such arrangement is further described later in association with at least FIGS. 14A-14B. In some examples, the axial array of conductive elements is not located on an outer surface of a housing of the microstimulation therapy device, but forms a structure extending outwardly from the housing of the therapy device. In one aspect, one such arrangement is further described later in association with at least FIGS. 17A-17C.

As shown in FIG. 13, one coupling arrangement includes a radial array coupling arrangement 432 in which an array of electrically conductive elements is arranged in an arcuate pattern to be spaced apart and extend about a circumference of a target nerve. In one aspect, the electrically conductive elements may be considered to be radially arranged to the extent that each electrically conductive element is positioned at the end of a virtual radius from a center point (e.g. a center of the cross-section of the nerve), with the ends of the virtual radii spaced apart from each other about a circumference of the nerve.

In some examples, the radial array of conductive elements is deployed as part of a structure extending outwardly from the housing of the therapy device, such as at least one flange of a pair of flanges used to mechanically couple the therapy device relative to the target nerve. In one aspect, one such arrangement is further described later in association with at least FIGS. 15A-15B.

As shown in FIG. 13, one coupling arrangement includes a grid array coupling arrangement 434 in which an array of electrically conductive elements is arranged in a grid. In some examples, the grid array of conductive elements forms a structure extending outwardly from the housing of the therapy device, such as a paddle extending about a portion of the target nerve. In one aspect, one such arrangement is further described later in association with at least FIGS. 16A-16B. However, in some examples, the grid array of conductive elements is located on an outer surface of the housing of the microstimulation therapy device. In one aspect, one such arrangement is further described later in association with at least FIGS. 18A-18B.

It will be understood that at least some of the examples of mechanical coupling arrangements (FIG. 12) may be combined with at least some examples of electrical coupling arrangements (FIG. 13). Moreover, in some examples, more than one electrical coupling arrangement may be implemented and in some examples, more than one mechanical coupling arrangement may be implemented. In other words, in some examples, at least some of the various mechanical are not mutually exclusive and at least some of the various electrical coupling arrangements are not mutually exclusive.

Figure 14A:
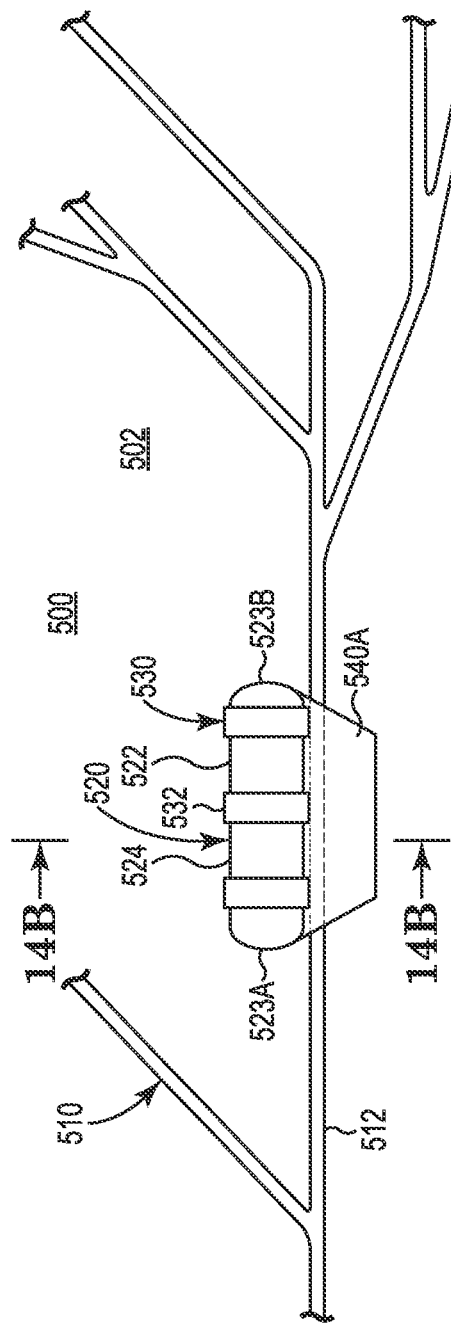
FIG. 14A is a diagram schematically representing a microstimulation therapy device implanted relative to a nerve, according to one example of the present disclosure.

FIG. 14A is a diagram 500 schematically representing a microstimulation therapy device 520 implanted relative to a nerve 512 of array 510 of nerves within a subcutaneous, extravascular environment 502, according to one example of the present disclosure. In some examples the microstimulation therapy device 520 comprises at least some of substantially the same features and attributes as the previously described microstimulation therapy devices 100, 200. As shown in FIG. 14A, therapy device 520 includes a housing 522 extending between opposite ends 523A, 523B with housing 522 having a generally electrically non-conductive outer surface 524. Housing 522 contains a stimulator (100, 200 in FIGS. 5, 8) and may sometimes be referred to as defining or including a body of the therapy device 520.

An array 530 of three ring electrodes 532 are arranged in an axially spaced apart manner along a length of the housing 522. In some examples, a fewer number or greater number of ring electrodes 532 may be used. In some examples, the electrodes 532 may be implemented as partial ring electrodes 532, and thus not extend about a complete circumference of the housing 522 provided that at least a portion of the respective partial ring electrodes 522 can establish contact against the nerve 512.

In some examples, the non-conductive area of the housing 522 defines a first portion. Each respective electrode 532 defines one of three second portions, each of which is surrounded by the non-conductive first portion.

Figure 14B:
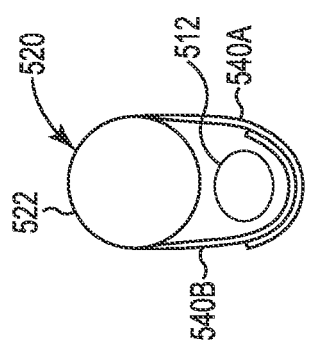
FIG. 14B is a sectional view schematically representing the implanted microstimulation therapy device of FIG. 14A, according to one example of the present disclosure.

As further shown in FIG. 14B, a pair of flanges 540A, 540B extend outwardly from the housing 522 of therapy device 520 and are biased to encircle and releasably engage nerve 512 to mechanically (and directly) secure the housing 522 relative to, and in contact against, nerve 512 such that electrodes 532 become directly electrically coupled relative to the nerve 512 (e.g. nerve bundle). In some instances, the flanges 540A, 540B may be sometimes be referred to as wrapping around or about the nerve 512. In some examples, each flange 540A, 540B may sometimes be referred to as an at least partially flexible element. In some examples, the flanges 540A, 540B are made from a polymer material, such as but not limited to a polyurethane material or one of several biocompatible materials, alone or in combination. In at least some examples, this arrangement enables application of stimulation therapy for treating sleep disordered breathing (SDB).

In some examples, the housing 522 of therapy device 520 has a length at least two times a diameter or width of the housing 522 with the elongate configuration enhancing stability of the housing 522 when secured against nerve 512.

In some examples, the body 522 has a volume less than about cubic centimeters.

With general reference to at least FIGS. 14A-14B, in some examples, housing 522 of microstimulation therapy device 520 has opposite ends 523A, 523B formed of electrically non-conductive material, and therefore in some examples, no electrical transmission of stimulation pulse occurs through the ends 523A, 523B of housing 522.

With further general reference to at least FIGS. 14A-14B, in some examples, the housing 522 of microstimulation therapy device 520 has opposite ends 523A, 523B devoid of fixation elements. In other words, in such examples the housing 522 lacks any mechanical element (such as but not limited to a screw) protruding axially from end of housing 522 or otherwise configured at end(s) of housing 522 for fixating solely the end of the housing 522 relative to a bony structure.

With further general reference to FIGS. 14A-14B, in some examples, housing 522 of microstimulation therapy device 520 is not invasively fixed relative to the tissue (e.g. nerve 512) to which electrical stimulation is to be applied and/or is located remotely from the muscle targeted for contraction. Accordingly, in some instances, the housing 522 may sometimes be referred to as being non-nerve-invasively secured or being non-invasively secured relative to the nerve to be electrically stimulated.

In sharp contrast to at least some examples of the present disclosure, some commercially available implantable stimulators are attached to the to-be-stimulated tissue (e.g. cardiac wall) via a screw which is invasively implanted within the to-be-stimulated tissue (e.g. cardiac wall), where a to-be-stimulated tissue is a muscle targeted for contraction. In such examples, the fixation mechanism penetrates the tissue to which electrical stimulation is applied.

In sharp contrast to some commercially available injectable stimulators, the housing 522 of therapy device 520 (of at least some examples of the present disclosure) is secured relative to the tissue (e.g. nerve) to be stimulated, thereby minimizing and/or avoiding migration while enhancing patient comfort.

With further general reference to at least FIGS. 14A-14B, in some examples, a contact interface between housing 522 of the microstimulation therapy device 520 and nerve 512 does not define a primary securing interface. Instead, the flanges 540A, 540B extending outward from the housing 522 primarily define a securing interface relative to the nerve with the flanges 540A, 540B omitting any electrically conductive elements. In some examples, suture loops may be installed to further secure the flanges 540A, 540B in their closed position about the nerve 512.

However, in some examples, a differently shaped housing may be substituted for the generally cylindrical shaped housing 522. For instance, housing 522 may be replaced with a housing 1522 having an external surface with an arcuate nerve-engaging portion, such as described and illustrated in association with at least FIGS. 19A-20B. With such an arrangement, the arcuate shape of the nerve-engaging portion enhances maintaining a stable, secure position of the housing 1522 relative to the nerve. In this way, the housing 1522 complements the action of flanges 540A, 540B in securing the stimulation therapy device 520 relative to nerve 512.

FIG. 15A is a diagram 600 schematically representing a microstimulation therapy device 620 implanted relative to a nerve 512 of array 510 of nerves within a subcutaneous, extravascular environment 502, according to one example of the present disclosure. In some examples, the microstimulation therapy device 620 comprises at least some of substantially the same features and attributes as the previously described microstimulation therapy devices 100, 200 and/or therapy device 520 (FIGS. 14A-14B). As shown in FIG. 15A, therapy device 620 includes a housing 622 extending between opposite ends 623A, 623B with housing 622 having a generally electrically non-conductive outer surface 624. In some examples, no electrically conductive elements (such as ring electrodes 532 in FIG. 14A) are present on external surface 624. However, in some examples, the entire external surface 624 or substantially the entire external surface 624 can be electrically conductive and serve as a single electrode.

As shown in both FIGS. 15A-15B, a pair of flanges 640A, 640B extends outwardly from the housing 622 of therapy device 620 and are biased to encircle and releasably engage nerve 512 to mechanically (and directly) secure the housing 622 relative to, and in contact against, nerve 512 such that electrodes 644 on the flange 640B become directly electrically coupled relative to the nerve 512. In one aspect, the array 642 of electrodes 644 are spaced apart from each other and arranged in a radial pattern along the length of the flanges 640A, 640B to at least partially surround or encircle the circumference of the nerve 512 for applying a stimulation therapy to treat sleep disordered breathing (SDB). Accordingly, in some examples, the array 642 provides one example implementation of the radial array 432 in FIG. 13.

It will be understood that housing 622 contains a stimulator (e.g. 100, 200 in FIGS. 5, 8) and that an electrical connection extends from the stimulation circuitry (within housing 622) through the flange 640B to the respective electrodes 644 and/or through flange 640A if some electrodes 644 are located on flange 640A. In some examples, each electrode 644 may be independently controlled in applying a stimulation signal to the nerve 512. As noted elsewhere, in at least some examples, the stimulator is encapsulated within non-conductive material within the housing 622.

In one aspect, the housing 622 of microstimulation therapy device 620 is held directly against nerve 512 (which is to be stimulated) even though no stimulation is applied via the external surface 624 of the housing 622 of the therapy device 620. As previously described in association with at least FIGS. 14A-14B, the housing 622 may be substituted for a housing having a concave, arcuate cross-sectional shape which betters conforms or complements the arcuate outer surface of the nerve 512. One such substitute housing may correspond to the housing in at least the example(s) later described and illustrated in association with at least FIGS. 19A-20B.

With general reference to at least some examples of FIGS. 15A-15B, no electrically conductive element extends axially beyond either end 623A, 623B of the housing 622. In one aspect, this arrangement gives the therapy device 620 (including electrodes 644) a small footprint. In one aspect, this small footprint may enable a small electromagnetic footprint, at least in the sense that less heating may result from the relatively short lead loop length, thereby mitigating potential nerve damage that might otherwise occur in the presence of relatively larger lead loop lengths. In addition, this arrangement may minimize and/or avoid a patient-to-patient variability that commonly occurs in routing a lead in pectorally implanted therapy devices, in which such patient-to-patient variability may produce uncertainty in MR-conditional testing. Accordingly, at least some examples of the present disclosure, such as at least the arrangement in FIGS. 15A-15B, may enable a microstimulation therapy device to receive a MR-conditional rating, in which the patient may be eligible for at least some types of MR scanning.

With general reference to at least some examples of FIGS. 14A-14B, 15A-15B, in some implementations, the flanges (540A, 540B in FIGS. 14A-14B; 640A, 640B in FIGS. 15A-15B) do not extend a distance from the housing 522, 622 more than a length of housing 522, 622.

With general reference to at least some examples of FIGS. 15A-15, in its closed position, the electrically conductive portions of the flange 640B do not extend a distance from the housing 622 more than a diameter of nerve 512 or more than a diameter of the housing 622.

Figure 16A:
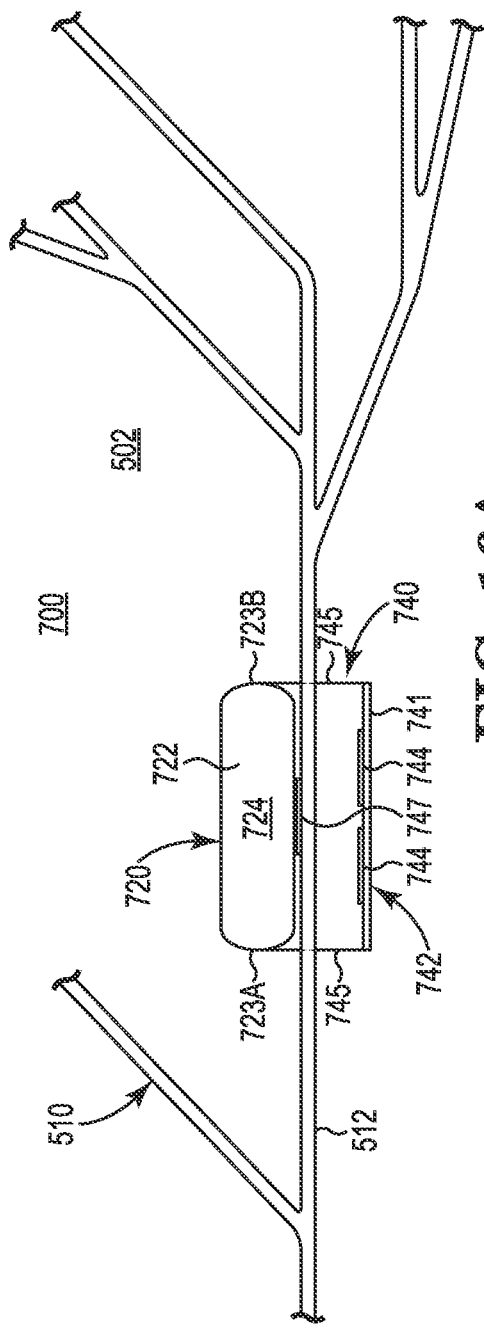
FIG. 16A is a diagram schematically representing a microstimulation therapy device implanted relative to a nerve, according to one example of the present disclosure.

FIG. 16A is a diagram 700 schematically representing a microstimulation therapy device 720 implanted relative to a nerve 512 of array 510 of nerves within a subcutaneous, extravascular environment 502, according to one example of the present disclosure. In some examples, the microstimulation therapy device 720 comprises at least some of substantially the same features and attributes as the previously described microstimulation therapy devices 100, 200. As shown in FIG. 16A, therapy device 720 includes a housing 722 extending between opposite ends 723A, 723B with housing 722 having a generally electrically non-conductive surface 724. In some examples, at least one electrically conductive element (e.g. an electrode 747) is located on surface 724 in a position to directly engage nerve 512 when housing 722 is secured relative to nerve 512.

Figure 16B:
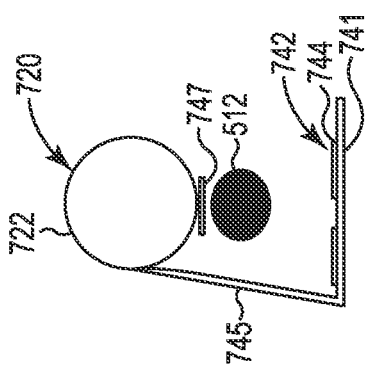
FIG. 16B is a sectional view schematically representing the implanted microstimulation therapy device of FIG. 16A, according to one example of the present disclosure.

As further shown in FIGS. 16A-16B, a paddle 741 supports a grid array 742 of electrodes 744, which face nerve 512 and which are opposite the electrode 747 on housing 722 thereby creating an arrangement in which various electrical vectors may be established across/though nerve 512. Via independent programming of the various electrodes 744, 747, stimulation electrical vectors may be established among and between the electrodes 744 on paddle 741 and/or stimulation electrical vectors may be established between electrode 747 and at least one of the electrodes 744 on paddle 741. The paddle 741 is supported by arm(s) 745 which extend outwardly from housing 722 of therapy device 720 by a distance to place the paddle 741 on an opposite side of the nerve 512 from housing 722 (and therefore electrode 747). The grid array 742 may comprise a 2×2, 3×3, etc. array of independently programmable electrodes 744.

In some examples, this arrangement is secured within the subcutaneous environment 502 and/or relative to nerve 512 via mechanical tines (similar to FIG. 18B). Alternatively, in some examples the arrangement in FIGS. 16A-16B can be secured relative to nerve 512 or another structure within subcutaneous environment 502 via a suture affixed directly on the stimulator housing 722 or affixed on a separate arm extends from housing 722.

It will be understood that the schematic representation in FIG. 16A-16B provides generous spacing between the paddle 741 and nerve 512 for illustrative clarity, but in at least some examples, in practice the arm 745 has a size (e.g. length) and/or shape to cause the paddle 741 (and electrodes 744 thereon) to be in releasable contact against nerve 512 to at least partially secure the device 720 relative to the nerve 512 and to implement operative electrical coupling of the electrodes 747, 744 relative to nerve 512.

FIG. 17A is a diagram 800 schematically representing a microstimulation therapy device 820 implanted relative to a nerve 512 of array 510 of nerves within a subcutaneous, extravascular environment 502, according to one example of the present disclosure. In some examples, the microstimulation therapy device 820 comprises at least some of substantially the same features and attributes as the previously described microstimulation therapy devices 100, 200. As shown in FIG. 17A, therapy device 820 includes a housing 822 extending between opposite ends 823A, 823B with housing 822 having a generally electrically non-conductive outer surface 824. In some examples, at least one electrically conductive element (e.g. an electrode 847) is located on outer surface 824 in a position to directly engage nerve 512 when housing 822 is secured relative to nerve 512. In some examples, the entire surface or substantially the entire surface 824 can be electrically conductive and thereby serve as a single electrode As further shown in FIG. 17A, one end 849A of a corkscrew-shaped flange 848 extends axially from one end 823B of housing 822 and supports an axially spaced apart array 842 of electrodes 844, which wrap about a surface of nerve 512. In some examples, the flange 848 may sometimes be referred to as being helical. In some examples, flange 848 is biased to self-wrap about nerve 512, which is further schematically depicted in FIG. 17B, thereby placing the electrodes 844 in direct contact against nerve 512. FIG. 17C provides further information 850 regarding at least some examples associated with the arrangement of FIGS. 17A-17B.

In one aspect, at least the biasing force and self-wrapping behavior of the helical flange 848 at least partially secures the electrodes 844 relative to the nerve and at least partially secures the housing 822 of the therapy device 820 relative to the nerve 512. In some examples, mechanical tines (similar to FIG. 18B) can be used to further secure the housing 822 relative to nerve 512. Alternatively, in some examples the arrangement in FIGS. 17A-17B can be secured relative to nerve 512 or another structure within subcutaneous environment 502 via a suture affixed directly on the stimulator housing 822 or affixed on a separate arm extends from housing 822. Accordingly, these arrangements act to further secure the housing 822 relative to the nerve 512 and/or relative to the subcutaneous environment 502 to facilitate direct engagement of electrode 847 on housing 822 against nerve 512.

Via independent programming of the various electrodes 844, 847, stimulation electrical vectors may be established among and between the electrodes 844 on flange 848 and/or stimulation electrical vectors may be established between electrode 847 (on housing 822) and at least one of the electrodes 844 on flange 848.

While FIG. 17A-17B provide one schematic representation of the helical flange 848 in relation to nerve to illustrate the axial spacing of the electrodes, extension from housing, etc., FIGS. 17C-17D provide a further schematic representation to more fully illustrate the helical configuration of flange 848 and to illustrate that in at least some examples, the flange 848 may have a width (W2) generally corresponding to or greater than a width (W1) of the electrodes 844 located on or forming part of flange 848. As shown in at least FIG. 17D, in some examples the electrodes 844 are located on an inner, nerve-engaging surface 845 of flange 848 and that outer surface 843 lacks such electrodes 844 (in at least some examples).

Moreover, it will be understood that the generous spacing shown in FIG. 17A between the flange 848 (including electrodes 844 thereon) and nerve 512 is provided for illustrative clarity and that in practice the flange 848 would directly contact and releasably engage the nerve 512, such as depicted in at least FIG. 17B.

In some examples, the device 820 may comprise more than one helical flange 848, such as having two such flanges extend from opposite ends of the housing 822. In some examples, both flanges 848 comprise at least one electrode along the length of the respective flange. However, in some examples, just one of the flanges 848 includes at least one electrode along its length, as shown in FIGS. 17A-17D.

In some examples, the housing 822 is positioned to contact nerve 512 even when the housing 822 omits an electrode 847.

In some examples, housing 822 omits electrode 847 and is not in contact with nerve. In some such examples, housing 822 is secured relative to a non-nerve structure, which may be some distance from nerve 512. In such examples, the flange 848 may have a length sufficient to extend from the housing 822 to the nerve 512 while still permitting a more distal portion of the flange 848 to engage nerve 512 both mechanically and electrically via electrodes 844. It will be understood in some such examples that an electrical connection extends through the length of flange 848 between the stimulator in housing 822 and the electrodes 844.

Figure 21A:
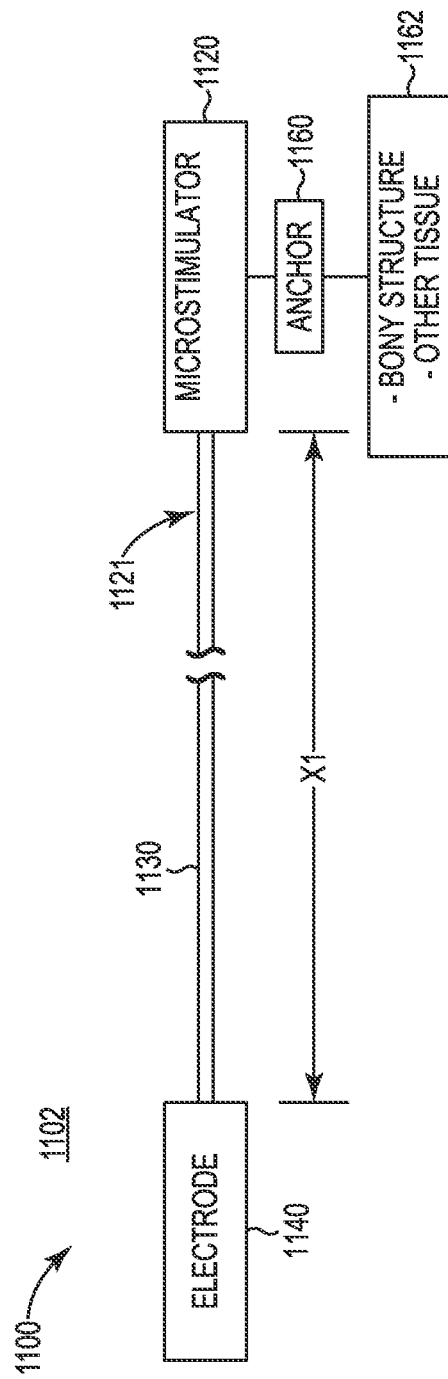
FIG. 21A is a diagram schematically representing a microstimulation therapy device, according to one example of the present disclosure.
Figure 21B:
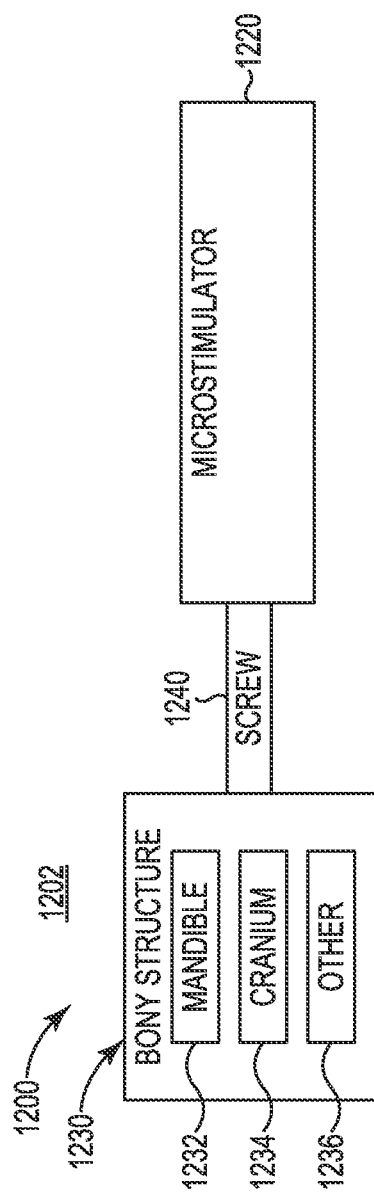
FIG. 21B is a diagram schematically representing an implanted microstimulation therapy device secured relative to a bony structure, according to one example of the present disclosure.

In some examples, at least some of the above-described examples associated with the device 820 of FIGS. 17A-17D may be implemented via and/or complement at least some of the examples associated with the arrangement(s) described and illustrated in association with at least FIG. 21A and/or FIG. 21B. Accordingly, various features associated with the arrangements in FIGS. 17A-17D, 21A and/or 21B may be combined in a complementary manner.

FIG. 18A is a diagram 900 schematically representing a microstimulation therapy device 920 implanted relative to a nerve 512 of array 510 of nerves within a subcutaneous, extravascular environment 502, according to one example of the present disclosure. In some examples, the microstimulation therapy device 920 comprises at least some of substantially the same features and attributes as the previously described microstimulation therapy devices 100, 200. As shown in FIGS. 18A-18B, therapy device 920 includes a housing 922 extending between opposite ends 923A, 923B and opposite side edges 924A, 924B. In one aspect, housing 922 has a generally electrically non-conductive surface 924 supporting an array 945 of electrically conductive elements 947 (e.g. electrodes) for stimulating nerve 512 when housing 922 is secured relative to nerve 512, as shown in FIG. 18C.

As further shown in FIGS. 18A-18C, an array 925 of tines 926 extend from the housing 922 to facilitate mechanical fixation of the therapy device 920 relative to the subcutaneous environment 502 in a manner to juxtapose electrodes 947 in close proximity and/or contact against nerve 512. In some examples, tines 926 are positioned at and extend from the opposite side edges 924A, 924B of housing 922. In some examples, each tine is biased to extend in a particular orientation adapted to facilitate fixation within the subcutaneous environment 502. While FIGS. 18A-18C depict tines 926 having a particular orientation, it will be understood that tines 926 may be formed, attached, or constructed with any orientation within a generally 360 degree orientation depending upon the particular fixation scheme. In some examples, all of the tines 926 have the same general orientation (e.g. angle) while in some examples, at least some of the tines 926 have an angle/orientation different than at least some other tines 926. FIG. 18D provides further information 950 regarding at least some examples associated with the arrangement of FIGS. 18A-18C.

Among other features, the housing 922 of therapy device 920 in FIGS. 18A-18C is provided in a generally planar shape having minimal thickness, which may enhance implantation by maintaining a relatively low profile. Moreover, in some examples, the housing 922 has a width extending between side edges 924A, 924B that is substantially greater (e.g. 2×, 3×, etc.) than a diameter of the nerve 512, thereby providing enhanced lateral stability upon deployment of tines 926.

With general reference to at least some examples associated with at least FIGS. 14A-18D as well as at least FIGS. 19A-20B, the compact arrangement in which the housing of a stimulator of the microstimulation therapy device is located directly against the target nerve or in proximity to the nerve (as opposed to a pectoral location of a pulse generator) may enhance patient comfort and ease surgical implantation.

In at least some examples of the microstimulation therapy device described throughout the present disclosure, such as but not limited to, FIGS. 5, 8, and 14A-18B, at least some of the electronics (e.g. circuitry, components, elements) within the housing of the stimulator of microstimulation therapy device 100, 200 and/or at least some electronic components external to the housing of the stimulator of therapy device 100,200 may be implemented as integrated passive devices on silicon, via chip stacking, and/or via flexible substrates.

In at least some examples of the microstimulation therapy device described throughout the present disclosure, such as but not limited to, FIGS. 5, 8, 14A-18B, and 19A-20C at least some examples of the housing of the stimulator of microstimulation therapy device 100, 200 includes: (A) feedthroughs mounted directly onto a printed circuit board (PCB) or electronics package; (B) feedthroughs connected to electronics via a process similar to solder reflow once there is direct contact between the feedthroughs and the board; and/or (C) active or smart lead technology that allows one or two feedthroughs to be multiplexed outside of the hermetic sealed assembly.

In at least some examples of the microstimulation therapy device described throughout the present disclosure, such as but not limited to, FIGS. 5, 8, 14A-18B, and 19A-20C, at least some examples of the electrodes external to the housing of the stimulator microstimulation therapy device include at least the following characteristics. For instance, in some examples an electrode structure (e.g. a lead) is integrated with the hermetically sealed housing, such as at least partially depicted in at least FIGS. 15B, 16B, 17A-17B in which a proximal end of a structure carrying electrodes (which are spaced apart from the housing) is electrically and mechanically coupled relative to (and extending outwardly from) the hermetic housing.

In another instance, in some examples, at least some electrodes are mounted directly on the hermetic housing so the housing acts like a paddle lead, such as at least partially depicted in FIGS. 14A and 16A-18A, 19A-19C. In some such examples in which such electrodes form an array of electrodes, these electrodes can be attached to the electronics package (within housing) with a direct contact process like that used for electronics surface mount technologies (SMT) to avoid the need to utilize space for larger interconnect technologies like printed circuit board (PCB) through-hole soldering.

In another instance, in some examples in which at least a portion of the outer surface of the housing is not conductive, conductive traces (e.g. ceramic) and electrodes could be directly integrated into the housing so the housing could be used to distribute stimulation and/or sensing signals from the electronic package within the housing to electrode arrays along the housing or on an electrode structure or lead extending from the housing.

In some examples, at least the stimulation circuitry of a stimulator comprises flexible circuitry. In some such examples, a power element is not incorporated within such flexible circuitry. In some such examples, the power element is located along a centerline of a housing containing the flexible stimulation circuitry, and in some instances, this centerline may sometimes be referred to as a spine of the housing.

Figure 19A:
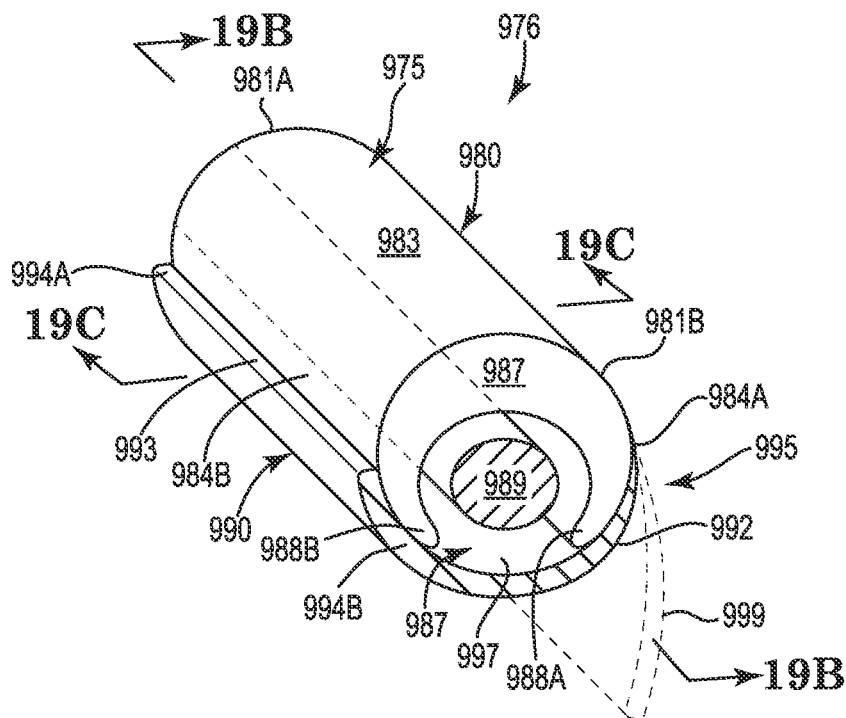
FIG. 19A is a perspective view schematically representing an electrode cuff of a stimulation therapy device, according to one example of the present disclosure.

FIG. 19A is a perspective view schematically representing a cuff electrode 975 of a stimulation therapy device 976, according to one example of the present disclosure.

As shown in FIG. 19A, cuff electrode 975 comprises a housing 980 to contain at least some features and attributes of a stimulator (e.g. 100 in FIG. 5; 200 in FIG. 8) with housing 980 having an arcuate nerve-engaging surface 982 shaped (e.g. an arcuate cross-sectional shape) to correspond to an arcuate outer surface (e.g. circumference) of a nerve 989. The arcuate nerve-engaging surface 982 facilitates robust, secure engagement of the housing 980 relative to nerve 989. Housing 980 extends between a first end 981A and an opposite second end 981B. In some examples, housing 980 comprises a non-engaging surface 983 opposite the nerve-engaging surface 982. In some examples, the non-nerve-engaging surface 983 comprises an arcuate cross-sectional shape. In some examples, this arcuate cross-sectional shape of non-nerve-engaging surface corresponds to the arcuate cross-sectional shape of the nerve-engaging surface 982.

In some examples, the housing 980 may comprise a generally uniform thickness over at least 50 percent of a cross-sectional area of the housing 980.

In some examples, cuff electrode 975 comprises a flange 990. The flange 990 comprises a first side portion 992 extending from a first side 984A of an outer surface 983 of housing 982 and an opposite second side portion 993 releasably engageable relative to an opposite second side 984B of outer surface 983 of housing 982. The flange 990 has a generally arcuate cross-sectional shape including a nerve-engaging surface 997 sized to extend across the opening 987 defined between opposite end portions 988A, 988B of housing 980.

In some examples, the flange 990 is a separate member and the first side portion 992 of flange 990 is then secured relative to the first side 984A of housing 982. However, in some examples, the first side portion 992 of flange 990 is molded with housing 982 such that housing 980 and flange 990 together form a single unitary molded piece (e.g. a monolithic structure).

In either case, the first side portion 992 of flange 990 is flexibly bendable relative to first side 984A of housing 982 to enable moving the flange 990 between a closed position (represented in FIG. 19A via solid lines) covering the opening 987 between end portions 988A, 988B of housing 980 and an open position (represented via dashed lines 999) pivoted away from opening 987 to permit maneuvering the housing 982 on and off the nerve 989 during implantation. In some examples, the flexibly bendable functionality may sometimes be referred to as being a living hinge.

In some examples, in cooperation with first side 984A of housing 982, the flange 990 is biased in the closed position (represented by solid lines) but can be moved into the open position to mount or dismount the relative to the nerve 989.

In some examples, cuff electrode 975 forms at least a portion of a therapy device having at least some of substantially the same features and attributes as therapy device 520 in FIGS. 14A-14B. In some examples, cuff electrode 975 comprises at least a partial implementation of the therapy device 520 of FIGS. 14A-14B. However, in the example shown in FIG. 19A, the therapy device 975 comprises just one flange 990 instead of two flanges 540A, 540B in FIG. 14A-14B. However, it will be understood that in some examples, instead of having a single flange 990, cuff electrode 975 may include two flanges 990 oriented in opposite directions to at least partially overlap each other.

In addition, in the example shown in FIG. 19A, the cuff electrode 975 omits ring electrodes 532 on housing 980 and instead provides at least one electrode on nerve-engaging surface 982 while omitting electrodes on outer surface 983 (e.g. a non-nerve engaging surface) of housing 980. For illustrative clarity, the at least one electrode is omitted from FIG. 19A.

Figure 19B:
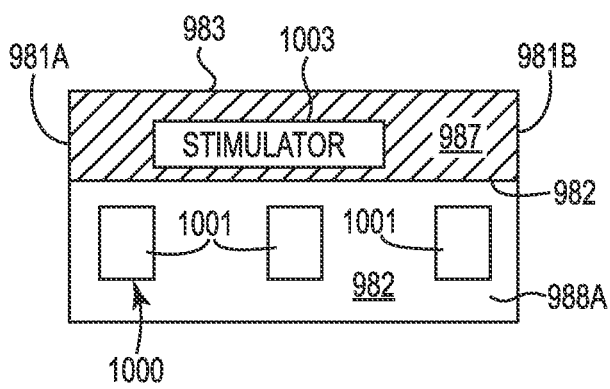
FIG. 19B is a sectional view as taken along lines 19B-19B in FIG. 19A, which schematically represents a cuff electrode, according to one example of the present disclosure.
Figure 19C:
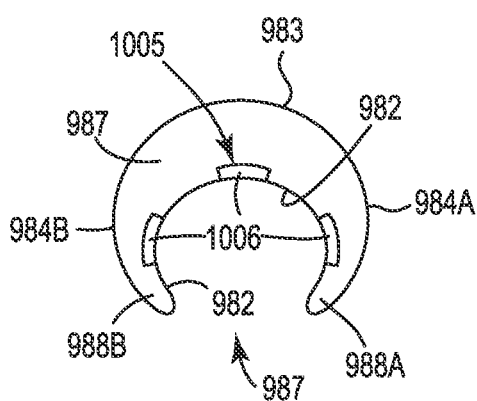
FIG. 19C is a sectional view as taken along lines 19C-19C in FIG. 19A, which schematically represents a cuff electrode, according to one example of the present disclosure.

However, as shown in the sectional views of FIGS. 19B and 19C, in some examples the at least one electrode comprises an array 1000 of electrodes 1001. In some examples, as shown in FIG. 19B, the electrodes 1001 may be axially spaced apart along a length (L) nerve-engaging surface 982 of the housing 980. In some examples, as shown in FIG. 19B, an array 1005 of electrodes 1006 may be spaced apart in a radial pattern extending transversely along nerve-engaging surface 982. In some examples, the at least one electrode may comprise a grid array like that in FIGS. 18A-18B such that both axially spaced apart electrodes 1001 and radially spaced apart electrodes 1005 are present in a grid (e.g. 2×2, 3×3, etc.) on nerve-engaging surface 982. In some examples, other than having different locations, there is no difference between the functionality of electrodes 1001 as compared to electrodes 1005, with any various combination of electrodes 1001 and/or electrodes 1005 functioning in a complementary manner. In some examples, electrodes 1001 and/or electrodes 1005 are independently programmable to implement a neurostimulation therapy.

In some examples, just a single electrode 1001 or 1005 is located on nerve-engaging surface 982. In some such examples, cuff electrode 975 comprises additional electrodes, such as on nerve-engaging surface 997 of flange 990, which function in a complementary manner with the single electrode (1001 or 1005) on nerve-engaging surface 982.

In some examples, the at least one electrode of cuff electrode 975 is located on the nerve-engaging surface 997 of flange 990 instead of on nerve-engaging surface 982 of the housing 982. In some examples, the at least one electrode on nerve-engaging surface 997 may comprise an axially spaced apart array 1000 of electrodes 1001 as shown in the sectional view of FIG. 19B and/or a radially spaced apart array 1005 of electrodes 1005 as shown in the sectional view of FIG. 19C.

In some examples, both the nerve-engaging surface 982 of housing 980 and the nerve-engaging surface 997 of flange 990 include at least one electrode (e.g. 1001 or 1005), which may be a single electrode on each respective nerve-engaging surface 982, 997 or which may be an array (1000 and/or 1005) of electrodes on each of nerve-engaging surface 982, 997

It will be understood that the schematic representation in FIG. 19A provides generous spacing between an outer surface of nerve 989 and the nerve-engaging surface 982 (of housing 980) and nerve-engaging surface 997 (of flange 990) for illustrative clarity. However, in at least some examples, in practice the housing 980 and/or flange 990 are sized and shaped to, cause nerve-engaging surfaces 982, 997 to directly contact and releasably engage the arcuate outer surface of nerve 989 to grippingly secure the cuff electrode 975 about the nerve 989.

In some examples, at least a portion of the housing 980 and/or flange 990 comprises a flexible, resilient material which may enable at least one of the nerve-engaging surfaces 982, 997 to at least partially conform about the nerve 989 to more securely engage the nerve 989.

As further shown in the sectional view of FIG. 19B, in some examples housing 980 comprises a body 987 internal to outer surface 983 and nerve-engaging surface 982. In some examples, as schematically represented via FIG. 19B, a stimulator 1003 (e.g. 100, 200 in FIGS. 5, 8) is located within body 987 and thereby contained within housing 980. It will be understood that in some examples, the various elements comprising a stimulator 1003 may be distributed throughout body 987 and are not necessarily consolidated in a single monolithic structure. The stimulator 1003 is electrically connected to the electrodes 1001 (or 1005 in FIG. 19C) via body 987 so that nerve-engaging surface 982 is non-conductive except of the surfaces of electrodes 1001, 1005.

Figure 20A:
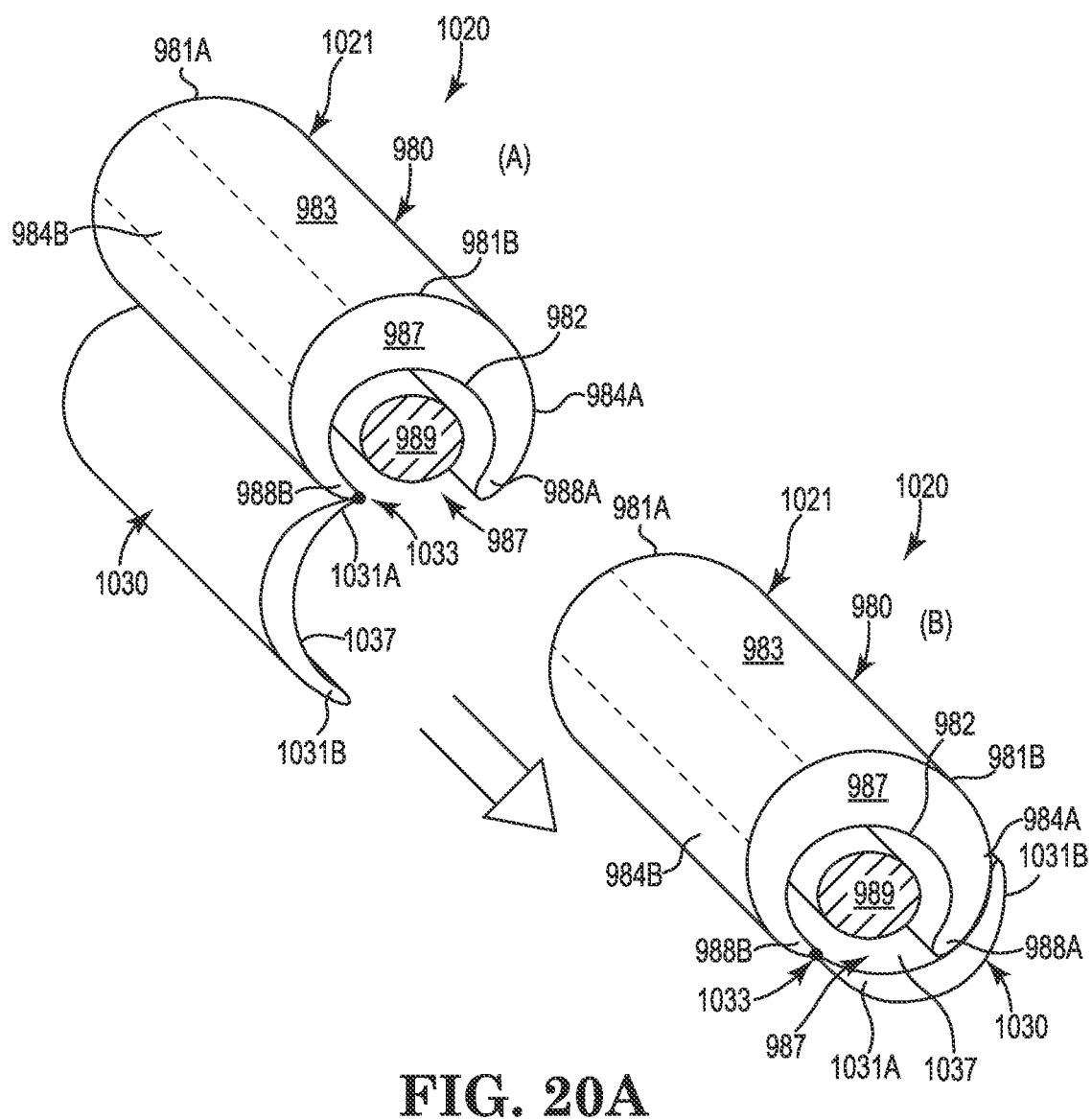
FIG. 20A is a perspective view schematically representing an electrode cuff for a stimulation therapy device, according to one example of the present disclosure.

FIG. 20A is a perspective view schematically representing a cuff electrode 1021 of a stimulation therapy device 1020 in an open position (A) and a closed position (B), according to one example of the present disclosure.

In some examples, the cuff electrode 1021 comprises at least some of substantially the same features as cuff electrode 975 with a few exceptions. In one exception, cuff electrode 1021 provides a flange 1030 like flange 990 except with a hinge 1033 at a junction of an end portion 988B of the housing 982 and an end portion 1031A of flange 1030. In some examples the flange 1030 comprises a generally rigid member. In some examples, flange 1030 comprises a semi-rigid, resilient member. In view of the end-to-end connection of the flange 1030 relative to the housing, the flange 1030 may sometimes be referred to as a cover.

Together with hinge 1033, this cover 1030 may sometimes be referred to as a closable clasp which releasably locks into the closed position (B) in which end portion 1031B of flange 1030 is firmly engaged against end portion 988A of housing 982. Accordingly, in some examples, the hinge 1033 permits rotation of cover 1030 between the open and closed position, with cover 1030 biased to remain in the closed position until or unless a sufficient force is applied to overcoming the biasing force of hinge 1033 such that the cover 1030 moves to the open position (A).

In some examples, the structure and functionality of hinge 1033 is implemented via a shape memory material formed as part of housing 982 and/or flange 1030, and with such material extending between and/or forming the junction of the end portion 988B of housing 982 and end portion 1031A of flange 1030. In some examples, the shape memory material may comprise a metal material such as, but not limited to, Nitinol while in some examples, the shape memory material may comprise a non-metal material.

In some examples of the cuff electrode 1021 of FIG. 20A, the axial array of electrodes 1001 (FIG. 19B) and/or the radial array of electrodes 1005 (FIG. 19C) may be implemented on a nerve-engaging surface 982 of the housing 980. In some examples, the axial array of electrodes 1001 (FIG. 19B) and/or the radial array of electrodes 1005 (FIG. 19C) may be implemented on a nerve-engaging surface 1037 of the flange 1030. In some examples, both respective nerve-engaging surfaces 982, 1037 includes at least some electrodes, whether in the axial array configuration (FIG. 19B), the radial array configuration (FIG. 19C), or some other combination of electrodes.

FIG. 20B is a perspective view schematically representing a cuff electrode 1051 of a stimulation therapy device 1050, according to one example of the present disclosure. In some examples, the cuff electrode 1051 comprises at least some of substantially the same features and attributes as the stimulators of the therapy devices described in association with FIGS. 1-18 and/or in association with FIG. 21A-25B. In some examples, the cuff electrode 1051 comprises one example implementation of at least some of the features and attributes of the therapy device described in association with at least FIG. 14A-14B or 15A-15B.

In some examples, cuff electrode 1051 comprises a housing 1060 defining a nerve-engaging surface 1062, including a first nerve-engaging portion 1065, a pair of second nerve-engaging portions 1067A, 1067B, and a third pair of nerve-engaging portions 1069A, 1069B. In one aspect, these various nerve-engaging portions 1065, 1067A, 1067B, 1069A, 1069B work together to releasably engage a nerve 989. In some examples, the portion of cuff electrode 1051 including nerve-engaging portions 1067A, 1067B, and 1069A, 1069B may sometimes be referred to as arms 1059A, 1059B which extend from a body 1064 of housing 1060. In some examples, in their open position (A), the arms 1059A, 1059B may extend generally parallel to each other, or even diverge from each other to provide an ample opening 1087 to mount and dismount cuff electrode 1051 relative to nerve 989 such as during implantation, etc.

In a manner similar to that shown in FIG. 19B, body 1064 may contain (e.g. encapsulate) a stimulator (e.g. at least 100, 200 in FIGS. 5, 8 1003 in FIG. 19B). As noted elsewhere and as applicable to any of the examples of the present disclosure, in some examples, except for any electrodes present on a nerve-engaging surface of the housing 1060, the entire external surface 1063 of housing 1060 defines a non-conductive surface. As noted elsewhere and as applicable to any of the examples of the present disclosure, in some examples body 1064 comprises a non-conductive material in which the stimulator is contained or encapsulated internally within housing 1060.

In some examples, the respective pivot portions 1071A, 1071B and pivot portions 1070A, 1070B permit rotation of end portions 1088A, 1088B of arms 1059A, 1059B between the open position (A) and closed position (B). Once cuff electrode 1051 is installed onto nerve 989 in a closed position (B), the arms 1059A, 1059B are biased to remain in the closed position (B) until or unless a sufficient force is applied to overcoming the biasing force of hinge 1033 such that the end portions 1088A, 1088B move to the open position (A). However, it will be understood that the open position (A) may be typically employed primarily during initial implantation and maneuvering of the cuff electrode 1051 relative to nerve 989.

In some examples, the structure and functionality of pivot portions 1070A, 1070B, 1071A, and 1071B may be implemented via a shape memory material formed as part of housing 1060. In some examples, the shape memory material may comprise a metal material such as, but not limited to, Nitinol while in some examples, the shape memory material may comprise a non-metal material In some examples, at least some of the pivot portions 1070A, 1070B, 1071A, 1071B may be sometimes be referred to as a living hinge.

While not shown in FIG. 20B, in some examples, the first nerve-engaging portion 1065 of housing 1060 comprises an arcuate shaped surface in a manner similar to nerve-engaging surface 982 of housing 980 in FIGS. 19A-19C. In some examples, the respective second nerve-engaging portions 1067A, 1067B of housing 1060 comprise an arcuate shaped surface in a manner similar to nerve-engaging surface 982 of housing 980 in FIGS. 19A-19C. In some examples, the respective third nerve-engaging portions 1069A, 1069B of housing 1060 comprise an arcuate shaped surface in a manner similar to nerve-engaging surface 982 of housing 980 in FIGS. 19A-19C.

In some examples, the respective first, second and third nerve-engaging surfaces 1065, 1067A, 1067B, 1069A, 1069B have a contour which gradually blends into the adjacent respective nerve-engaging surface such that the respective first, second, and third nerve-engaging surfaces do not act as discretely different surfaces.

In some examples, the cuff electrode 1051 provides an arrangement in which the arms 1059A, 1059B and body 1064 form a single unitary piece (e.g. a monolithic element) which can releasably engage a nerve.

FIG. 20C is a partial end view schematically representing two arms of cuff electrode 1090 for a microstimulation therapy device 1060, according to one example of the present disclosure. As shown in FIG. 20C, the two end portions 1088A, 1088B of arms 1059A, 1059B point toward each other, and even may contact in some examples. In some examples, the two end portions 1088A, 1088B may even overlap.

In some examples of the cuff electrode 1061 of FIG. 20B, the axial array of electrodes 1001 (FIG. 19B) and/or the radial array of electrodes 1005 (FIG. 19C) may be implemented on a nerve-engaging surface 1062 of the housing 1060, whether on portion 1065, portions 1067A, 1067B, and/or portions 1069A, 1069B.

FIG. 21A is a diagram 1100 schematically representing a microstimulation therapy device 1120 implantable relative to a nerve within a subcutaneous, extravascular environment 1102, according to one example of the present disclosure. In some examples, the microstimulation therapy device 1120 comprises at least some of substantially the same features and attributes as the previously described microstimulation therapy devices 100, 200.

As shown in some examples, the microstimulation therapy device 1120 forms part of an arrangement 1121 including a lead 1130 and a cuff electrode 1140.

In general terms, cuff electrode 1140 includes some non-conductive structures biased to (or otherwise configurable to) releasably secure the cuff electrode 1140 about a target nerve 30 (FIGS. 1-4) and includes an array of electrodes to deliver a stimulation signal to the target nerve. In some examples, the cuff electrode 1140 may comprise at least some of substantially the same features and attributes as described within at least U.S. Pat. No. 8,340,785 issued on Dec. 25, 2012 and/or U.S. Patent Publication 2011/0147046 published on Jun. 23, 2011.

The lead 1130 extends between the cuff electrode 1140 and microstimulator 1120 with lead 1130 having a length (X1). In some examples, length X1 may be up to 20 centimeters to enable anchoring the microstimulator to a bony structure (or other sturdy tissue) a short distance from the target nerve and cuff electrode 1140. In some examples, length X1 may be 10 centimeters or less for other anchoring arrangements and/or electrode cuff deployments.

As further shown in FIG. 21A, the arrangement 1121 may further include an anchor(s) 1160 by which microstimulator 1120 is secured relative to a bodily structure 1162 (e.g. bony structure or other sturdy tissue) within the subcutaneous environment 1102. In some examples, the anchor 1160 may include a loop element to facilitate deployment of fastening mechanism relative to the bodily structure 1162.

FIG. 21B is a diagram 1200 schematically representing an implanted microstimulation therapy device 1220 secured relative to a bony structure 1230 within a subcutaneous environment 1202, according to one example of the present disclosure. In some examples, the microstimulation therapy device 1220 comprises at least some of substantially the same features and attributes as the previously described microstimulation therapy devices 100, 200. As shown in FIG. 21B, a screw 1240 or analogous mechanical fastener fixes the microstimulator 1220 against a bony structure 1230, which may be a mandible 1232, cranium 1234, or other bony tissue 1236.

Figure 22:
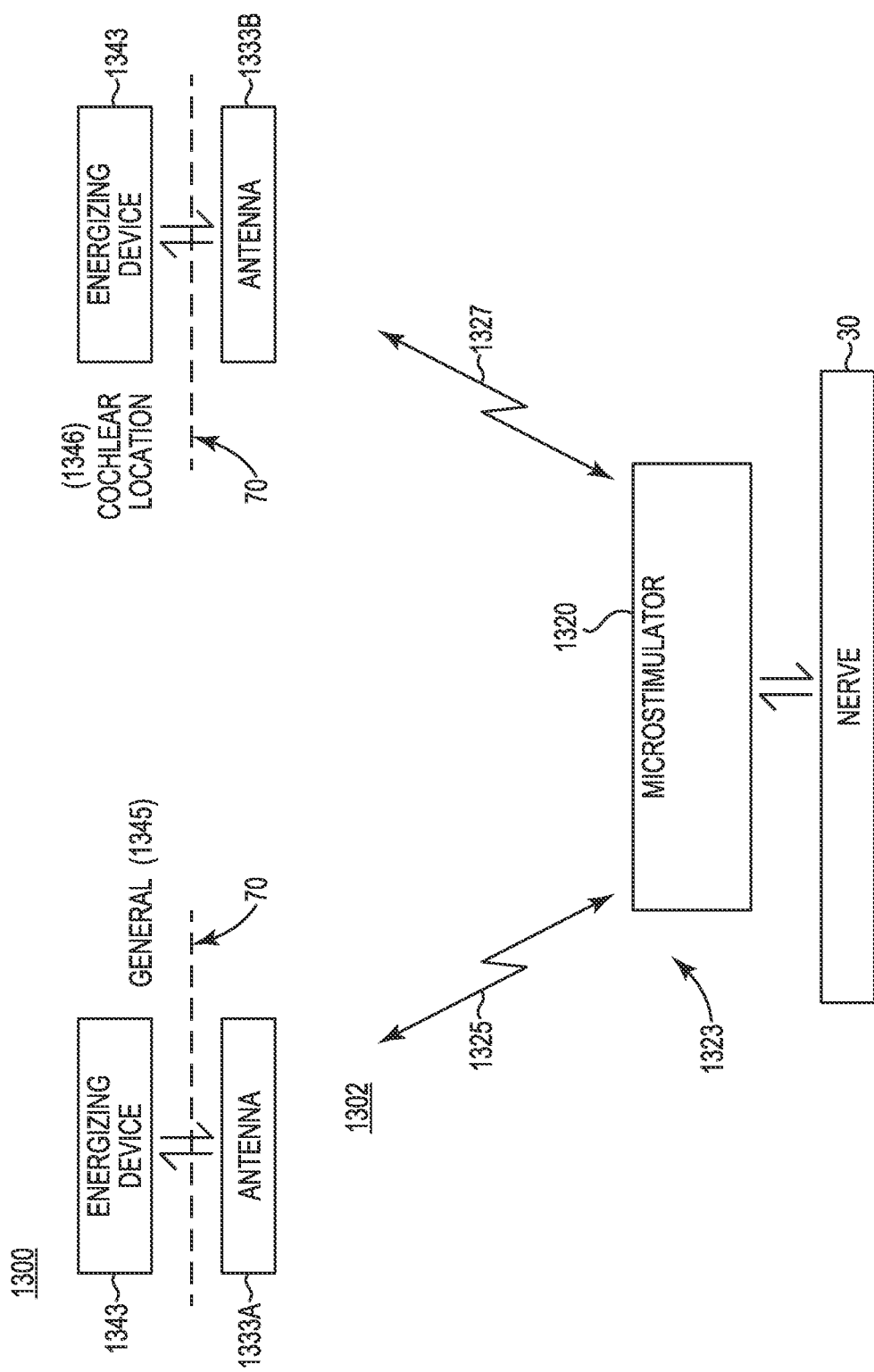
FIG. 22 is a diagram schematically representing antenna arrangements associated with a microstimulation therapy device, according to one example of the present disclosure.

FIG. 22 is a diagram 1300 schematically representing arrangements for an antenna associated with a microstimulation therapy device 1320, according to one example of the present disclosure. In some examples, the microstimulation therapy device 1320 comprises at least some of substantially the same features and attributes as the previously described microstimulation therapy devices 100, 200. In some examples, as shown in FIG. 22 in some examples, microstimulator 1320 forms part of an arrangement including an antenna 1333A or 1333B, and which may include other elements (e.g. lead, electrodes, anchors, etc.) as described throughout the present disclosure.

As shown in FIG. 22, in a manner at least consistent with at least some previously described examples, the microstimulator 1320 is electrically coupled and mechanically coupled relative to a nerve 30 for applying a therapeutic stimulation signal to nerve 30. Moreover, microstimulator 1320 receives energy via an antenna arranged to facilitate fast charging and/or energy harvesting protocols. Accordingly, in one arrangement an antenna 1333A is positioned (e.g. secured) within the subcutaneous environment 1302 close to skin 70 in a general location 1343 of the head/neck region so that the antenna 1333A is readily accessible by an externally located energizing device 1343 for charging and/or energy harvesting. In this arrangement, antenna 1333A is in electrical communication with microstimulator 1320 via a pathway 1325, which may be wired or wireless.

In another arrangement, an antenna 1333B is positioned (e.g. secured) within the subcutaneous environment 1302 close to skin 70 but in a cochlear location 1346 of the head/neck region so that the antenna 13336 is readily accessible by an externally located energizing device 1343 for charging and/or energy harvesting. In this arrangement, antenna 13336 is in electrical communication with microstimulator 130 via a pathway 1327, which may be a wired pathway.

In either arrangement, in some examples, the antenna is reasonably close to the skin to facilitate a fast rate of energy transfer relative to the energizing device 1343 and/or the antenna is relatively remote from the nerve 30 and/or microstimulator 1320.

It will be understood that in at least some examples, various features and attributes among the different examples throughout at least FIGS. 1-22 and/or throughout FIGS. 23A-27, may be combined in different configurations on a feature-by-feature manner.

It also will be understood that in the examples described throughout the present disclosure, at least any implantable elements exposed to tissue, fluids, etc. within the human body will be made of biocompatible materials, whether polymer and/or metal.

Figure 23A:
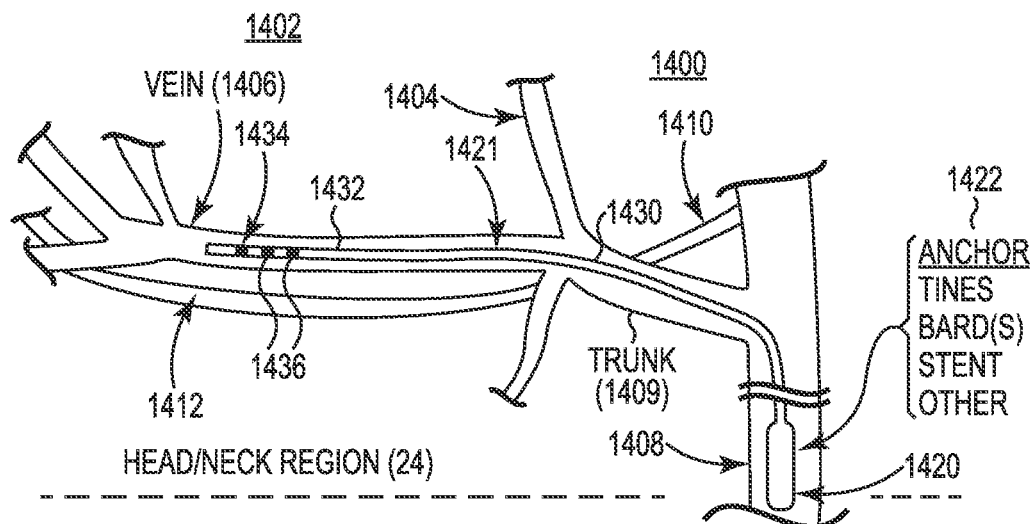
FIG. 23A is a diagram schematically representing a microstimulation therapy device implanted within at least a portion of the vasculature, according to one example of the present disclosure.

FIG. 23A is a diagram 1400 schematically representing a microstimulation therapy device 1420 implanted within at least a portion of the vasculature within a head/neck region 24, according to one example of the present disclosure. In some examples, the microstimulation therapy device 1420 comprises at least some of substantially the same features and attributes as the previously described microstimulation therapy devices 100, 200.

As shown in FIG. 23A, microstimulation therapy device 1420 forms part of an arrangement 1421 also including a lead 1430 and an electrode array 1434. The lead 1430 extends distally from a housing of the therapy device 1420 and with a distal portion 1432 of the lead 1430 supporting the electrode array 1434 of electrodes 1436. In some examples, the array 1434 includes several axially spaced apart electrodes 1436, although other electrode configurations may be used.

As shown in FIG. 23A, microstimulation therapy device 1420 has been implanted such that the entire arrangement 1421 resides within the vasculature 1404, with distal electrode array 1434 positioned within a vein 1406 adjacent a target nerve 1412 of an array 1410 of nerves, such that electrical stimulation may be applied to nerve 1412 from the intravascular location of the distal electrode array 1434. Accordingly, in some instances, such stimulation may sometimes be referred to as a transvascular application of a therapeutic stimulation signal.

In one aspect, in a manner similar to at least some examples previously described herein, the relatively small size and/or shape of the microstimulator device 1420 facilitates a minimally invasive implantation procedure in which the arrangement 1421 may be implanted within the vasculature 1404 within the head/neck region 24 without involving other parts of the patient's body. Accordingly, in some examples, the entire arrangement 1421 (including microstimulation therapy device 1420) resides entirely within the peripheral vasculature.

In some examples, the housing of the microstimulation therapy device 1420 is secured within the vasculature via an anchor 1422, which may comprise at least one of tines, barbs, stents, and/or other fixation mechanisms.

However, it will be understood that in some examples, the microstimulation therapy device 1420 may be secured within a more central portion of the patient's vasculature to accommodate some implementations in which a housing of the therapy device 1420 has a relatively larger size. As such, in some implementations, the therapy device 1420 may reside within a portion of the vasculature extending in a portion of the body other than the head/neck region.

Figure 23B:
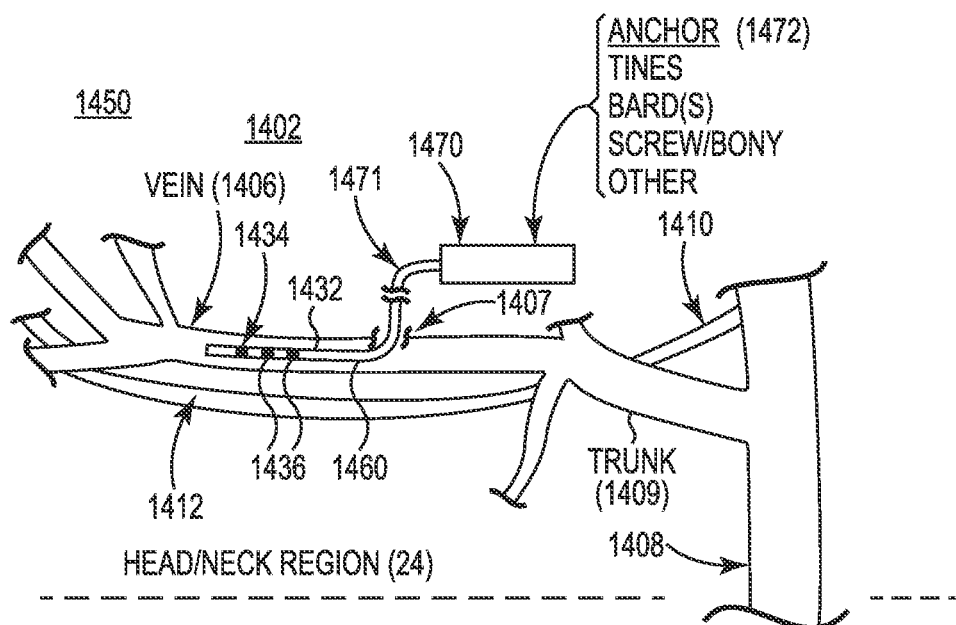
FIG. 23B is a diagram schematically representing a microstimulation therapy device implanted within at least a portion of the vasculature, according to one example of the present disclosure.

FIG. 23B is a diagram 1450 schematically representing a microstimulation therapy device 1470 implanted within at least a portion of the vasculature within a head/neck region, according to one example of the present disclosure. In some examples, the microstimulation therapy device 1470 comprises at least some of substantially the same features and attributes as the previously described microstimulation therapy devices 100, 200.

As shown in FIG. 23B, microstimulation therapy device 1470 forms part of an arrangement 1471 also including a lead 1460 and an electrode array 1434. The lead 1460 extends distally from a housing of the therapy device 1470 and with a distal portion 1432 of the lead 1460 supporting the electrode array 1434 of electrodes 1436. In some examples, the array 1434 includes several axially spaced apart electrodes 1436, although other electrode configurations may be used.

As shown in FIG. 23B, microstimulation therapy device 1470 has been implanted such that the just the distal electrode array 1434 (and a portion of lead 1460) resides within the vasculature 1404, and in particular within vein 1406 adjacent the target nerve 1412 of an array 1410 of nerves, such that electrical stimulation may be applied to nerve 1412 from the intravascular location of the distal electrode array 1434. Accordingly, in some instances, such stimulation may sometimes be referred to as a transvascular application of a therapeutic stimulation signal.

In some examples, the housing of the microstimulation therapy device 1470 is secured external to the vasculature 1404 within the subcutaneous environment 1402 via an anchor 1472, which may comprise at least one of tines, barbs, screws, and/or other fixation mechanisms. In some examples, when the anchor comprises a screw(s), the housing of the therapy device 1470 is secured relative to a bony structure, such as but not limited to, the mandible (either modified or unmodified), the cranium, and/or other bony structures suited to position the microstimulation therapy device 1470 in reasonably close proximity to the target nerve 1412 and vein 1406 in which lead 1460 and electrode array 1434 extend.

In one aspect, in a manner similar to at least some examples previously described herein, the relatively small size and/or shape of the microstimulator device 1470 facilitates a minimally invasive implantation procedure in which the arrangement 1471 may be implanted within the subcutaneous environment 1402 within the head/neck region 24 without involving other parts of the patient's body and via a location reasonably close the target nerve 412 to be stimulated. Accordingly, in some examples, the entire arrangement 1471 (including microstimulation therapy device 1420) resides entirely within head/neck region 24. In addition, the relatively small size of the microstimulation therapy device 1470 enables its subcutaneous implantation (via a percutaneous access or analogous minimally invasive technique) in a location reasonably close to the vascular entry point 1407 at which distal electrode array 1434 can be placed promptly adjacent the targeted nerve 1412, thereby saving much time and effort in achieving a therapeutically efficacious implantation.

FIG. 24 is a block diagram of a therapy manager 1600, according to one example of the present disclosure. In some examples, therapy manager 1600 may be implemented as therapy manager 122 in the therapy devices 100, 200 of FIGS. 5 and 8 and/or therapy manager 1600 comprises at least substantially the same features and attributes as therapy manager 122 in therapy devices 100, 200. In some examples, therapy manager 1600 is implemented as therapy manager 1705 in control portion 1700 in FIG. 25A and/or comprises at least some of substantially the same features and attributes as therapy manager 1705 in FIG. 25A. While not necessarily expressly stated directly in association with FIG. 24, it will be understood that therapy manager 1600 may utilize and/or coordinate with at least some of the therapy-related features, functions, attributes, parameters, etc. as described throughout at least some examples of the present disclosure.

In some examples, at least some of the features and functions of therapy manager 1600 are accessed via user interface 1710 in FIG. 25B.

As shown in FIG. 24, in some examples, therapy manager 1600 includes a stimulation intensity function 1610, an open loop module 1620, and a closed loop module 1630.

In some examples, once therapy is initiated during a daily treatment period, stimulation is performed generally continuously. In some examples, once therapy is initiated during a daily sleep period, stimulation is performed on an "as-needed" basis, such that stimulation occurs when needed but is otherwise suspended.

In some examples, the open loop module 1620 causes a microstimulation therapy device to apply therapeutic stimulation without receiving and/or sensing physiologic information.

In some examples, the closed loop module 1630 causes a microstimulation therapy device to apply therapeutic stimulation, at least in part, based on received and/or sensed physiologic information related to the intended therapy. As shown in FIG. 24, in some examples the close loop module 1630 includes a stimulation timing function 1640, an automatic stimulation on/off function 1650, a respiratory information parameter 1660, an auto-titrate function 1662, a power management function 1664, and/or a sleep position parameter 1670.

In some examples, via at least stimulation timing function 1640, stimulation is synchronized relative to a sensed onset of inspiration in the respiratory cycle. In some instances, via at least stimulation timing function 1640 initiation, termination, and/or duration of stimulation are based on a sensed respiratory waveform but are not synchronized relative to each inspiratory phase.

However, in some instances, via at least stimulation timing function 1640, stimulation is generally synchronized with inspiration.

In some instances, via at least stimulation timing function 1640, whether or not stimulation is synchronized with inspiration, stimulation is triggered according to a time sequence at least partially based on at least one of a beginning of inspiration, an end of inspiration, a beginning of expiration, and/or an end of expiration.

In some examples, via an automatic stimulation state function 1650, stimulation is enabled and disabled (e.g. turned on and off) automatically according to various parameters. In some examples, such parameters include posture, respiratory rate, apnea-hypopnea event count, etc. However, in some examples, because sleep disordered breathing is generally associated with sleep periods of the patient, in some examples a treatment period automatically coincides with a daily sleep period of the patient with the automatic stimulation state function 1650 then enabling/disabling stimulation according to the above-identified parameters. In some instances, the daily sleep period is identified via sensing technology which detects motion, activity, posture, position of the patient, as well as other indicia, such as heart rate, breathing patterns, etc. However, in some instances, the daily sleep period is selectably preset, such from 10 pm to 6 am or other suitable times.

In some examples, the respiratory information parameter 1660 includes respiratory waveform information and/or tracks respiratory effort including respiratory patterns (e.g., inspiration, expiration, respiratory pause, etc.) and is obtained via a sensing function (e.g. 205 in FIG. 8). In some examples, this respiratory information is employed to trigger activation of stimulation circuitry (e.g. 112 in FIG. 8) to stimulate a target nerve (e.g. 30 in FIGS. 1-4) and/or is employed in various ways as described throughout at least some examples of the present disclosure.

In some examples, via at least the power management parameter 1664, a characteristic of a sensed respiratory waveform (e.g. via respiratory information parameter 1660) is used to reduce at least one parameter regarding an intensity of stimulation pulses (per stimulation intensity function 1610) to reduce power requirements. In some examples, such respiratory characteristics include apnea-hypopnea event detection, inspiratory onset detection, etc. In some examples, the at least one parameter of stimulation intensity function 1610 includes a pulse amplitude, number of pulses, pulse width, burst time, and/or electrode configuration.

In some examples, via at least the sleep position parameter 1670, the therapy manager includes a posture-adjustment function to enable adjusting stimulation timing (per 1640) and/or intensity (per 1610) in accordance with changing sleep postures/positions throughout the night.

In some examples, via an auto-titrate parameter 1662, a characteristic of a sensed respiratory waveform (per parameter 1660) enables performing an auto-titration protocol via at least one parameter of stimulation intensity (per function 1610). In some examples, such characteristics include apnea-hypopnea event detection, inspiratory onset detection, etc. In some examples, the at least one parameter of stimulation intensity (1610) includes a pulse amplitude, number of pulses, pulse width, burst time, and/or electrode configuration.

FIG. 25A is a block diagram schematically representing a control portion 1700, according to one example of the present disclosure. In some examples, control portion 1700 includes a controller 1702 and a memory 1704. In some examples, control portion 1700 provides one example implementation of a control portion forming a part of, or implementing, any one of managers, control portions, and/or therapy devices/systems, as represented throughout the present disclosure in association with FIGS. 1-23.

In general terms, controller 1702 of control portion 1700 comprises at least one processor 1703 and associated memories. The controller 1702 is electrically couplable to, and in communication with, memory 1704 to generate control signals to direct operation of at least some components of the systems, devices, components, functions, and/or modules described throughout the present disclosure. In some examples, these generated control signals include, but are not limited to, employing manager 1705 stored in memory 1704 to manage therapy for sleep disordered breathing in the manner described in at least some examples of the present disclosure. It will be further understood that control portion 1700 (or another control portion) may also be employed to operate general functions of the various therapy devices/systems described throughout the present disclosure.

In response to or based upon commands received via a user interface (e.g. user interface 1710 in FIG. 25B) and/or via machine readable instructions, controller 1702 generates control signals to implement therapy implementation, monitoring, and/or management in accordance with at least some of the previously described examples of the present disclosure. In some examples, controller 1702 is embodied in a general purpose computing device while in some examples, controller 1702 is incorporated into or associated with at least some of the associated components of the therapy devices and/or managers described throughout the present disclosure.

For purposes of this application, in reference to the controller 1702, the term "processor" shall mean a presently developed or future developed processor (or processing resources) that executes sequences of machine readable instructions contained in a memory. In some examples, execution of the sequences of machine readable instructions, such as those provided via memory 1704 of control portion 1700 cause the processor to perform actions, such as operating controller 1702 to implement sleep disordered breathing (SDS) therapy and/or monitoring, as generally described in (or consistent with) at least some examples of the present disclosure. The machine readable instructions may be loaded in a random access memory (RAM) for execution by the processor from their stored location in a read only memory (ROM), a mass storage device, or some other persistent storage (e.g., non-transitory tangible medium or non-volatile tangible medium, as represented by memory 1704. In some examples, memory 1704 comprises a computer readable tangible medium providing non-volatile storage of the machine readable instructions executable by a process of controller 1702. In other examples, hard wired circuitry may be used in place of or in combination with machine readable instructions to implement the functions described. For example, controller 1702 may be embodied as part of at least one application-specific integrated circuit (ASIC). In at least some examples, the controller 1702 is not limited to any specific combination of hardware circuitry and machine readable instructions, nor limited to any particular source for the machine readable instructions executed by the controller 1702.

FIG. 25B is a block diagram schematically representing user interface 1710, according to one example of the present disclosure. In some examples, user interface 1710 forms part or and/or is accessible via a device external to the patient and by which the microstimulation therapy device 100, 200 may be at least partially controlled and/or monitored. The external device hosing user interface 1710 may be a patient remote and/or a clinician portal.

In some examples, user interface 1710 comprises a user interface or other display that provides for the simultaneous display, activation, and/or operation of at least some of the various components, modules, functions, parameters, features, and attributes of manager (122 in FIGS. 5, 8; 1600 in FIG. 24) and/or control portion (120 in FIGS. 5, 8; 1700 in FIG. 25A). In some examples, at least some portions or aspects of the user interface 1710 are provided via a graphical user interface (GUI). In some examples, as shown in FIG. 25B, user interface 1710 includes display 1712 and input 1714.

In some instances, at least some examples of a microstimulation therapy device as described in association with at least FIGS. 1-25 may be employed to perform vagal nerve stimulation and/or baroreceptor-based therapy.

Figure 26:
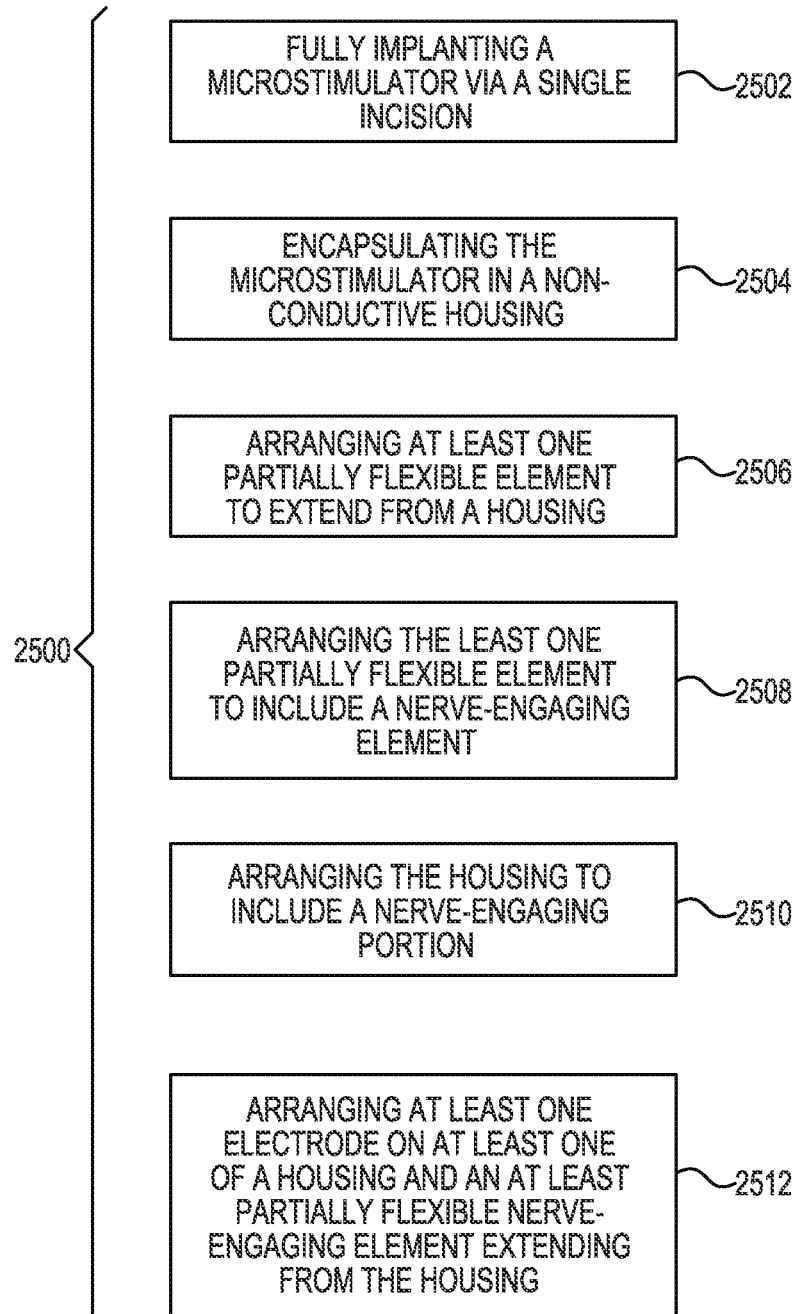
FIG. 26 is a flow diagram schematically representing aspects associated with a method for microstimulation, according to one example of the present disclosure.

FIG. 26 is a block diagram schematically representing aspects of a method 2500 of microstimulation, according to one example of the present disclosure. In some examples, at least some aspects of method 2500 may be implemented via at least some of the systems, apparatuses, devices, stimulators (including microstimulators), sensors, power elements, functions, parameters, components, elements, etc. as described throughout the examples of the present disclosure in association with FIGS. 1-25B. In some examples, at least some aspects of method 2500 may be implemented via at least some systems, apparatuses, devices, stimulators (including microstimulators), sensors, power elements, functions, parameters, components, elements, etc. other than those described throughout the examples of the present disclosure in association with FIGS. 1-25B.

As shown at 2502 in FIG. 26, in some examples one aspect of a method 2500 comprises fully implanting a microstimulator via single incision. As shown at 2504 in FIG. 26, in some examples one aspect of a method 2500 comprises encapsulating a microstimulator in a non-conductive portion of a housing. As shown at 2506 in FIG. 26, in some examples one aspect of a method 2500 comprises arranging at least one partially flexible element to extend from a housing. As shown at 2508 in FIG. 26, in some examples one aspect of a method 2500 comprises arranging the at least one partially flexible element to include a nerve-engaging element. As shown at 2510 in FIG. 26, in some examples one aspect of a method 2500 comprises arranging the housing to include a nerve-engaging portion. As shown at 2512 in FIG. 26, in some examples one aspect of a method 2500 comprises arranging at least one electrode on at least one of a housing and an at least partially flexible nerve-engaging element extending from the housing.

In some examples, the various aspects 2502-2512 may be performed together or in various combinations, with it being understood that any methods performed according to examples of the present disclosure are not limited to the aspects 2502-2512 associated with the method(s) implementable as schematically represented via FIG. 26.

Figure 27:
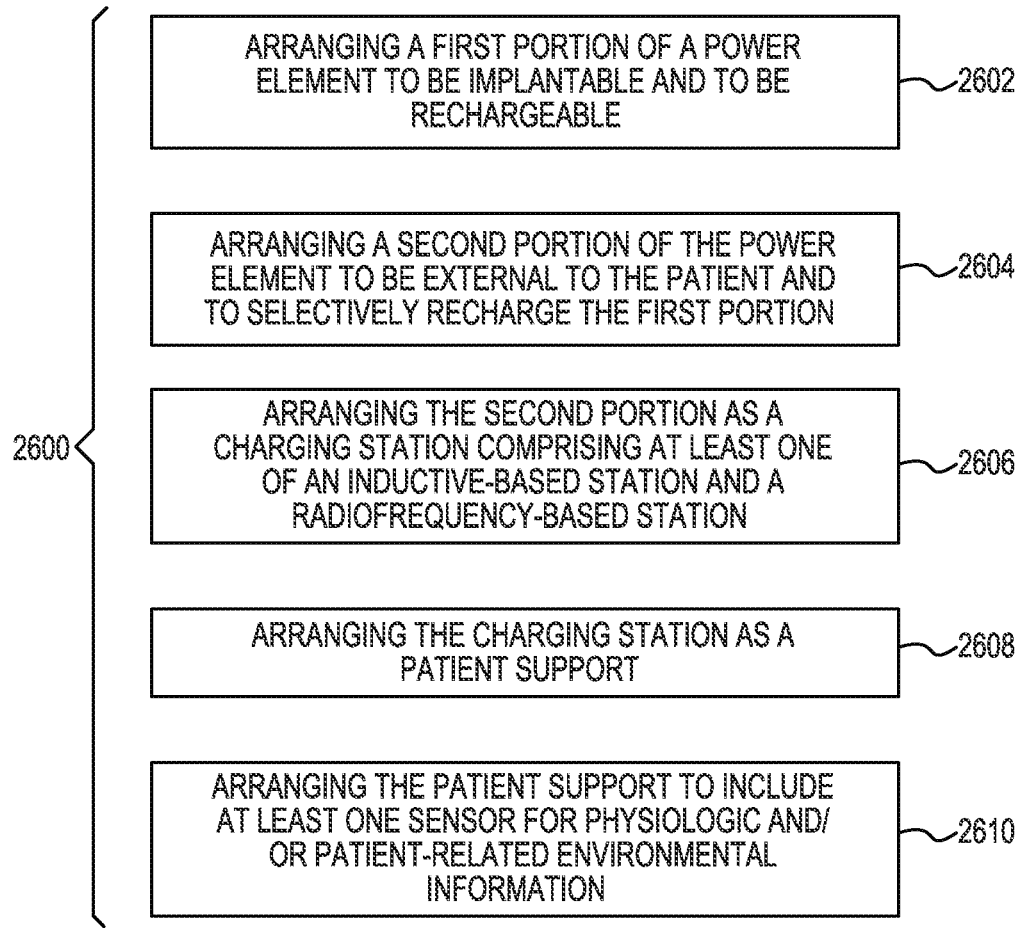
FIG. 27 is a block diagram schematically representing aspects associated with a method for microstimulation, according to one example of the present disclosure.

FIG. 27 is a block diagram schematically representing aspects of a method 2600 of microstimulation, according to one example of the present disclosure. In some examples, at least some aspects of method 2600 may be implemented via at least some of the systems, apparatuses, devices, stimulators (including microstimulators), sensors, power elements, functions, parameters, components, elements, etc. as described throughout the examples of the present disclosure in association with FIGS. 1-25B. In some examples, at least some aspects of method 2600 may be implemented via at least some systems, apparatuses, devices, stimulators (including microstimulators), sensors, power elements, functions, parameters, components, elements, etc. other than those described throughout the examples of the present disclosure in association with FIGS. 1-25B.

As shown at 2602 in FIG. 27, in some examples one aspect of a method 2600 comprises arranging a first portion of a power element to be implantable and to be rechargeable. As shown at 2604 in FIG. 27, in some examples one aspect of a method 2600 comprises arranging a second portion of the power element to be external to the patient and to selectively recharge the first portion. As shown at 2606 in FIG. 27, in some examples one aspect of a method 2600 comprises arranging the second portion as a charging station comprising at least one of an inductive-based station and a radiofrequency-based station. As shown at 2608 in FIG. 27, in some examples one aspect of a method 2600 comprises arranging the charging station as a patient support. As shown at 2610 in FIG. 27, in some examples one aspect of a method 2600 comprises arranging the patient support to include at least one sensor for physiologic and/or patient-related environmental information.

In some examples, the various aspects 2502-2512 may be performed together or in various combinations, with it being understood that any methods performed according to examples of the present disclosure are not limited to the aspects 2502-2512 associated with the method(s) implementable as schematically represented via FIG. 26.

Although specific examples have been illustrated and described herein, it will be appreciated by those of ordinary skill in the art that a variety of alternate and/or equivalent implementations may be substituted for the specific examples shown and described without departing from the scope of the present disclosure. This application is intended to cover any adaptations or variations of the specific examples discussed herein.

The invention claimed is:

1. A system comprising:
a therapy device arranged to be implanted within a head/neck region of a patient, comprising:
a microstimulator including a housing to encapsulate at least:
stimulation circuitry;
a rechargeable power element; and
a control portion including a therapy manager arranged to control the stimulation circuitry based on at least control information;
a stimulation electrode array; and
a flexible lead extending between, and electrically connecting, the stimulation electrode array and the microstimulator,
the therapy device being arranged to be implanted in a non-muscle, extravascular location with the stimulation electrode array coupled relative to a nerve to cause contraction of an upper-airway-patency muscle to treat obstructive sleep apnea;
a patient support external to the patient and including coils and an external power element;
at least one external sensor external to the patient to sense physiologic information comprising respiratory information, wherein the control information is based at least partially on the sensed respiratory information; and
a charging station external to the patient and adapted to wirelessly transmit to the microstimulator and via the coils:
power from the external power element to the rechargeable power element; and
the sensed physiologic information from the at least one external sensor.

2. The system of claim 1, wherein the charging station forms part of the patient support.

3. The system of claim 1, wherein the therapy device is sized to be fully implantable via a single incision.

4. The system of claim 1, wherein the housing includes a non-conductive material.

5. The system of claim 1, comprising a further electrode mounted on the housing.

6. The system of claim 1, wherein the patient support comprises the at least one external sensor, which comprises at least one of:
a pressure sensor;
an accelerometer; or
a piezoelectric sensor.

7. The system of claim 1, wherein the at least one external sensor comprises:
an airway position sensing arrangement;
an airflow sensing arrangement;
an airflow obstruction sensing arrangement;
a sleep disordered breathing (SDB) sensing arrangement to sense at least apneas and hypopneas;
a respiratory sensing arrangement; and/or
a body position sensing arrangement.

8. The system of claim 1, comprising a cuff electrode which includes the stimulation electrode array.

9. The system of claim 1, wherein the therapy device excludes a sensor.

10. The system of claim 1, wherein the therapy device comprises at least one internal sensor, which comprises at least one of:
an accelerometer;
an acoustic sensor;
an EMG sensor; or
a piezoelectric sensor.

11. The system of claim 1, wherein the charging station comprises a continuous charging function by which the external power element is to automatically charge the therapy device.

12. The system claim 1, wherein the rechargeable power element of the therapy device comprises a storage portion to store energy sufficient to apply stimulation therapy for at least one overnight therapy period, the system optionally comprising:
a hand-held external charging device adapted to transmit power to the rechargeable power element and to be received in the storage portion of the rechargeable power element of the therapy device.

13. The system of claim 1, wherein the therapy device comprises a mechanical fixation mechanism to secure the housing of the microstimulator within a subcutaneous environment of the patient relative to at least one of:
a non-nerve, non-bony structure, wherein the non-bony structure optionally comprises the digastric tendon; or
a non-nerve, bony structure.

14. The system of claim 1, wherein the patient support comprises the at least one external sensor and at least one of a bed, a pillow, or a neck support.

15. The system of claim 1, wherein the stimulation electrode array comprises at least three electrodes.

* * * * *